(12) United States Patent
Viovy et al.

(10) Patent No.: US 9,347,915 B2
(45) Date of Patent: May 24, 2016

(54) NON-THERMOSENSITIVE MEDIUM FOR ANALYZING SPECIES IN A CHANNEL AND FOR MINIMIZING ABSORPTION AND/OR ELECTROOSOMOSIC PHENOMENA

(71) Applicants: INSTITUTE CURIE, Paris (FR); CENTRE NATIONAL DE LA RECHERCHE SCIENTIFIQUE (C.N.R.S), Paris (FR)

(72) Inventors: Jean-Louis Viovy, Paris (FR); Valessa Barbier, Grenoble (FR)

(73) Assignees: Institute Curie, Paris (FR); Centre National de la Recherche Scientifique (C.N.R.S), Paris (FR)

(*) Notice: Subject to any disclaimer, the term of this patent is extended or adjusted under 35 U.S.C. 154(b) by 0 days.

(21) Appl. No.: 14/619,878

(22) Filed: Feb. 11, 2015

(65) Prior Publication Data

US 2015/0253285 A1 Sep. 10, 2015

Related U.S. Application Data

(63) Continuation of application No. 11/846,670, filed on Aug. 29, 2007, now Pat. No. 8,975,328, which is a continuation-in-part of application No. 10/312,537, filed as application No. PCT/FR01/02117 on Jul. 2, 2001, now abandoned, said application No. 11/846,670 is a continuation-in-part of application No. 10/312,538, filed as application No. PCT/FR01/02103 on Jun. 29, 2001, now abandoned.

(30) Foreign Application Priority Data

Jun. 30, 2000 (FR) ........................................ 00 08526
Jun. 30, 2000 (FR) ....................................... 00 08528

(51) Int. Cl.
*G01N 27/447* (2006.01)
*C08F 251/00* (2006.01)
*C08F 265/04* (2006.01)
*C08F 265/10* (2006.01)
*C08F 287/00* (2006.01)
*C08F 297/00* (2006.01)
*C08F 297/02* (2006.01)

(52) U.S. Cl.
CPC ........ *G01N 27/44747* (2013.01); *C08F 251/00* (2013.01); *C08F 265/04* (2013.01); *C08F 265/10* (2013.01); *C08F 287/00* (2013.01); *C08F 297/00* (2013.01); *C08F 297/026* (2013.01)

(58) Field of Classification Search
CPC .... C08F 251/00; C08F 265/04; C08F 265/10; C08F 287/00; C08F 297/00; C08F 297/026; G01N 27/44747
USPC ........................................... 524/504; 204/455
See application file for complete search history.

(56) References Cited

U.S. PATENT DOCUMENTS 6,162,877 A * 12/2000 Sau ..................... C08G 83/00
                                                              525/326.9

* cited by examiner

*Primary Examiner* — Ling Choi
*Assistant Examiner* — Chun-Cheng Wang
(74) *Attorney, Agent, or Firm* — Jones Robb, PLLC

(57) ABSTRACT

An aqueous liquid medium for analyzing, purifying or separating species in an element having walls or for treating the walls of an element. The medium includes at least a polymer consisting of several polymeric segments. The polymer is of the irregular block-copolymer or irregular comb-like polymer type and has on the average at least three junction points between polymeric segments of different chemical or topological nature. The medium may be used in methods for analyzing, purifying or separating species and methods for treating an element to be contacted with a fluid and/or species contained in the fluid during preservation, transport, analysis, purification or separation of the fluid.

1 Claim, 16 Drawing Sheets

NON-THERMOSENSITIVE MEDIUM FOR ANALYZING SPECIES IN A CHANNEL AND FOR MINIMIZING ABSORPTION AND/OR ELECTROOSOMOSIC PHENOMENA

CROSS REFERENCE TO RELATED APPLICATION

This application is a continuation of U.S. application Ser. No. 11/846,670 filed Aug. 29, 2007, which is a continuation-in-part application of U.S. application Ser. No. 10/312,537 filed Dec. 27, 2002 (now abandoned), which is a National Stage application of International PCT Application No. PCT/FR01/02117 filed Jul. 2, 2001, which claims priority to French application No. FR 00/08528 filed Jun. 30, 2000. U.S. application Ser. No. 11/846,670 also is a continuation-in-part application of U.S. application Ser. No. 10/312,538 filed Jul. 14, 2003 (now abandoned), which is a National Stage application of International PCT Application No. PCT/FR01/02103 filed Jun. 29, 2001, which claims priority to French application No. 00/08526, filed Jun. 30, 2000. The subject matter of each of the applications identified above is incorporated by reference in its entirety herein.

BACKGROUND OF THE INVENTION

The present invention relates to the field of techniques for analyzing, separating and purifying species, according to which it is necessary to migrate these species in a fluid known as the "separating medium".

It is also more particularly directed toward proposing a surface treatment solution which is of use in significantly reducing the nonspecific adsorption of species contained in this fluid to the walls of a channel or of a container containing said fluid.

According to a first aspect, the invention is more particularly directed toward proposing a separating medium that is suitable for separating species in channels or capillaries, at least one of the dimensions of which is submillimetric, and typically between 1 µm and 200 µm, for example 20 µm and 200 µm (referred to hereinbelow as microchannels). The invention in particular concerns methods for separating or analyzing biological macromolecules by capillary electrophoresis, by chromatography or by any method used in microchannels (capillary electrophoresis and capillary chromatography, microfluid systems, and "lab-on-chips"). The invention is particularly useful in the case of electrophoresis.

According to a second aspect the invention also relates more particularly to techniques for analyzing or for separating species, according to which it is necessary to transport said species in a channel, while at the same time minimizing the nonspecific interactions of said species, or of other components of said medium, with the walls of said channel or more generally with walls or solid elements present in said channel or said medium. These are in particular methods for separating or for analyzing biological macromolecules by capillary electrophoresis, by chromatography or by any method carried out in microchannels (microfluid systems, "laboratories on chips"). Examples of such systems are described, for example, in "Capillary electrophoresis in analytical biotechnology". Righetti ed., CRC press, 1996, or in J. Cheng et al. (1996), Molecular Diagnosis, 1, 183-200. The invention is of particular use in the case of electrophoresis.

The invention also relates to "hybridization" or "affinity" techniques in which the aim is to analyze, within a channel or a container, the species contained in a sample, as a function of their specific affinity for ligands contained in said channel or container, or attached to the walls of said container or said channel, at predetermined positions.

In the context of the invention, the term "nonspecific adsorption" is intended to be used as normally accepted by those skilled in the art, as an interaction of attraction between certain species or impurities contained in a sample and the walls of the container and of the channel which depends weakly or in an insufficiently controlled manner on the characteristics of said species or impurities. In the remainder of the text, the term "adsorption" or "nonspecific adsorption" will be used indifferently to denote the latter, as opposed to an interaction of specific affinity. The term "affinity" is intended to mean an interaction between a species and a substrate, the strength of which depends strongly on said species and on said substrate, and which, in any event, is sufficient to induce the separation or the identification of various species as a function of their biological or physicochemical characteristics.

For the purpose of the invention, the terms "solution for treating" and "treatment solution" are equivalent to the term "medium for treating".

In the text herein below, the expression "microfluid system" will denote any system in which fluids and/or species contained in a fluid are moved inside a channel or a set of channels, at least one of the dimensions of which is submillimetric, and the term "capillary electrophoresis (CE)" will denote microfluid systems in which the transportation of species is performed by the action of an electric field.

CE and microfluid systems allow faster separations with higher resolutions than the older methods of gel electrophoresis, do not require an anticonvective medium, and their properties have been used widely to perform separations of ions in liquid medium. At the present time, the vast majority of separations of biological macromolecules performed by CE use solutions of interlocked linear water-soluble polymers that have the advantage of being able to be replaced as often as necessary.

Many non-crosslinked polymers have been proposed as media for separating species inside a channel, in particular in the context of capillary electrophoresis. The choice of the best polymer for a given application depends on several parameters. For example, for the separation of analytes as a function of their sizes, it is necessary for the medium to present the analytes with sufficiently resistant topological obstacles (Viovy et al., Electrophoresis, 1993, 14, 322). This involves the separating medium being highly interlocked, and thus relatively viscous. It is also necessary for the polymers present in the separating medium not to undergo any interactions of attraction with the analytes. The reason for this is that interactions of this type give rise to a slowing-down of certain analytes, and to additional dispersion (H. Zhou et al. HPCE 2000, Saarbrucken, 20-24 Feb. 2000). Thus, it is well known that for DNA sequencing, or for protein separation, poorer results are obtained when the matrix has a more hydrophobic nature.

It has also been proposed in the literature to use copolymers as separating medium. In Menchen, WO 94/07133, it is proposed to use as separating medium in capillary electrophoresis, media comprising copolymers of block copolymer type which are said to be "regular" since they have hydrophilic segments of a selected and essentially uniform length and a plurality of regularly spaced hydrophobic segments, at a concentration higher than the overlap concentration between polymers. These media have the advantage of being shear-thinning, i.e. they can be introduced into a capillary under high pressure, while at the same time presenting solid topological obstacles in the absence of external pressure. Unfortunately, the media that may be used according to this principle are difficult to synthesize, which makes them expensive and limits the type of structures that may be envisaged. Also, these polymers are relatively hydrophobic, and their performance qualities for DNA sequencing, for example, are mediocre.

It has also been proposed to use as separating media thermosensitive media, the viscosity of which varies greatly during an increase in temperature. This type of medium has the advantage of allowing the injection of said medium into the capillary at a first temperature in a state of low viscosity, and the separation at a second temperature in a state of higher viscosity that displays good separation efficiency, as is commonly performed in gel electrophoresis, in particular with agarose. Patent applications WO 94/10561 and WO 95/30782 especially propose media that allow an easier injection by raising the temperature. In point of fact, said patent applications essentially describe microgels capable of decreasing in volume at high temperature (thus leading to a dilute solution of discontinuous particles of low viscosity) and of swelling at low temperature until they entirely fill the separating channel (thus giving the medium a gelled nature and good separating properties). Patent application WO 98/10274 itself proposes a molecular separating medium comprising at least one type of block copolymers that is in solution at a first temperature and in a gel-type state at a second temperature. The media described comprise triblock polymers of low molecular masses (typically less than 20,000), of the polyoxyethylene-polyoxypropyiene-polyoxyethylene (POE-Pop-POE) family and more specifically (POE99-POP69-POE99 in which the indices represent the number of monomers of each block) (trade name "Pluronic F127"). At low temperature, the two POE segments at the ends of the triblock systems are water-soluble and, given the low molecular mass of the copolymer, the solutions are relatively nonviscous up to a high concentration. By raising the temperature by about 15-25° C., the central POP segment becomes more hydrophobic, and these polymers become associated to form a gel-type state. However, this mechanism presents several drawbacks in electrophoresis. Firstly, it gives rise to a gel state that has good electrophoretic separating properties only at high polymer concentrations, of greater than 15 g/100 ml or even 20 g/100 ml, which leads to high friction and long migration times. Moreover, the dependence of the properties as a function of the rate of change of temperature makes the reproducibility of the results random. Finally, for many applications and in many devices, it is inconvenient, or even impossible, to change the temperature between the stage of filling of the channel and the separating stage.

In Madabhushi, U.S. Pat. No. 5,552,028, WO 95/16910 and 20 WO 95/16911, it is also proposed to use separating media comprising a screening medium and a surface-interaction component consisting of a polymer with wall-adsorption properties, with a molecular mass of between 5,000 and 1,000,000, of the disubstituted acrylamide polymer type. These matrices, and more particularly polydimethylacrylamide (PDMA), make it possible to reduce the electroosmosis and in certain applications, for instance sequencing, lead to good separating properties. However, they are relatively hydrophobic, which limits their performance qualities for certain applications, for instance DNA sequencing, and is even more harmful for other applications, for instance protein separation. Moreover, they lead to slow separations.

Consequently, despite the large number of studies and systems proposed, a medium that is optimum for all the various aspects of cost, of separation efficiency, of reduction of interactions with the walls and of convenience of use is not available at the present time for all the applications mentioned above.

In connection to uses of the invention for surface treatment, a major problem for all methods involving species within channels is the nonspecific adsorption of said species to the walls of said channels. This problem is particularly exacerbated in the case of channels of small dimensions and of biological macromolecules, the latter often being amphiphilic.

In the case of analytical methods, the consequence of this phenomenon of nonspecific adsorption to the walls by species contained in the sample or the fluid used to analyse said sample, is to delay certain analytes and to create an additional dispersion and therefore a loss of resolution. This adsorption may also give rise to a contamination of the channel walls, liable to affect the fluids intended to be subsequently introduced into this channel. Finally, if the analysis to be carried out on the species involves a specific interaction of the species with the separation medium, as in chromatography, electrochromatography or affinity electrophoresis methods, or with predetermined areas of the walls, as in hybridization methods such as "DNA chips" or "protein chips", or else with solid walls contained in the channel or container, as in methods of separation by affinity with latexes, these adsorption phenomena may compete with the desired specific interactions and interfere with or prevent the analysis.

Another limitation, which concerns more particularly electrokinetic separation methods, is electroosmosis, an overall movement of the separation medium due to the presence of charges on the walls of the capillary or of the channel. Since this movement is often variable over time and is not uniform, it is harmful to the reproducibility of the measurements and to the resolution. It is due to the charges which may be present at the surface of the capillary on account of its chemical structure, but may also be generated or increased by the adsorption onto the wall of charged species initially contained in the samples to be separated, and in particular proteins.

The present invention is more particularly concerned with the inhibition of these two phenomena, namely adsorption of species to the surfaces and/or electroosmosis.

Methods have already been proposed for combating electroosmosis and/or adsorption of species to surfaces. A first type of method involves treating the surface of the channel by adsorption of essentially neutral species, prior to the actual separation (Wiktorowicz et al., Electrophoresis, 11, 769, 1990, Tsuji et al., J. Chromatogr. 594, 317 (1992)). It has also been proposed to adsorb surface agents with a charge which is opposite to that of the wall, to reinforce the adhesion by electrostatic interactions.

In fact, these methods reduce electroosmosis to a certain degree, but they are relatively ineffective in preventing the adsorption of complex species of high molecular mass, such as, for example, proteins.

A more effective solution consists in irreversibly grafting an essentially neutral polymeric layer, such as acrylamide or polyvinyl alcohol, onto the walls, as described, for example, in U.S. Pat. No. 4,680,201, or alternatively U.S. Pat. No. 5,502,169 or U.S. Pat. No. 5,112,460. Ready-to-use treated capillaries are thus commercially available. These irreversibly treated capillaries give good reduction of electroosmosis for a certain number of separations. Unfortunately, they have a limited life span and are expensive.

It has also been proposed to use, in the separation medium, polymers with properties of adsorption to walls, such as methylcellulose (Hjerten, Chromatographic reviews, 9, 122, 1967) or polyvinylpyrrolidone (Mazzeo at al., Anal. Chem., 63, 2852, 1991). In application WO 98/10274, copolymers having affinity with walls of silica and capable of significantly reducing electroosmosis are proposed. The polymers described are triblock polymers of low molecular masses (typically less than 20,000), of the polyoxyethylene-polyoxypropylene-polyoxypropylene (POE-POP-POE) family. However, these polymers have a limited range of application. They require a change in temperature between the introduction into the capillary and the analytical phase, they only exert their beneficial effect at high concentrations, and they are also relatively hydrophobic, which makes them unsuitable for example for DNA sequencing. In addition, in these various methods of the prior art using polymers in the separation medium, the presence of the polymer is accompanied by a considerable variation in the physical properties, and in particular by a considerable increase in viscosity, which may pose problems for the introduction of fluid into the channel and for the separation properties themselves.

In U.S. Pat. No. 5,552,028 already cited above, it is also proposed to use separation media comprising a sieving medium and a surface interaction component consisting of a polymer with properties of adsorption to walls, having a molecular mass of between 5,000 and 1,000,000, of the disubstituted acrylamide polymer type. These matrices, and more particularly polydimethylacrylamide (PDMA), make it possible to reduce electroosmosis and, for some applications, such as sequencing, produce good separation properties. However, they are relatively hydrophobic, which limits their effectiveness for some applications such as DNA sequencing, and is even more harmful for other applications such as protein separation. Moreover, they produce slow separations.

Consequently, although many methods have been proposed for reducing adsorption to walls and/or electroosmosis, they are not found to be totally satisfactory.

BRIEF SUMMARY OF THE INVENTION

One object of the present invention according to its first aspect is, precisely, to propose the use of a family of polymers that is particularly advantageous as non-thermosensitive liquid separating medium for the separation, analysis or purification of species in channels.

More particularly, a subject of the present invention is a non-thermosensitive liquid medium for analyzing, purifying or separating species inside a channel, and comprising at least one polymer composed of several polymer segments, characterized in that said polymer is of the irregular block copolymer type or irregular comb polymer type and has on average at least three junction points established between polymer segments of different chemical or topological nature.

The object of the present invention is also, according to its second aspect, to provide a novel family of surface treatment solutions which are advantageous for minimizing the phenomena of nonspecific adsorption and of electroosmosis.

More particularly, a subject of the present invention is a solution for treating the surface of an element intended to be brought into contact with a fluid and/or species contained in this fluid during the transport, analysis, purification, separation or conservation of said fluid, characterized in that said solution comprises at least one polymer composed of several polymer segments, said polymer being of the block copolymer or comb polymer type and having on average at least three junction points between polymer segments which are chemically or topologically different in nature.

13a is polymer "PAM-PDMA-1" described in example 4 being added to the separation medium at a concentration by mass of 0.5%; the numbers above the peaks indicate the size of the corresponding DNA fragment.

13b is after treatment of the capillary for 2 hours with an aqueous solution containing 3% of the polymer PAM-PDMA described in example 11. The numbers above the peaks indicate the size of the corresponding DNA fragment.

Figure 14:
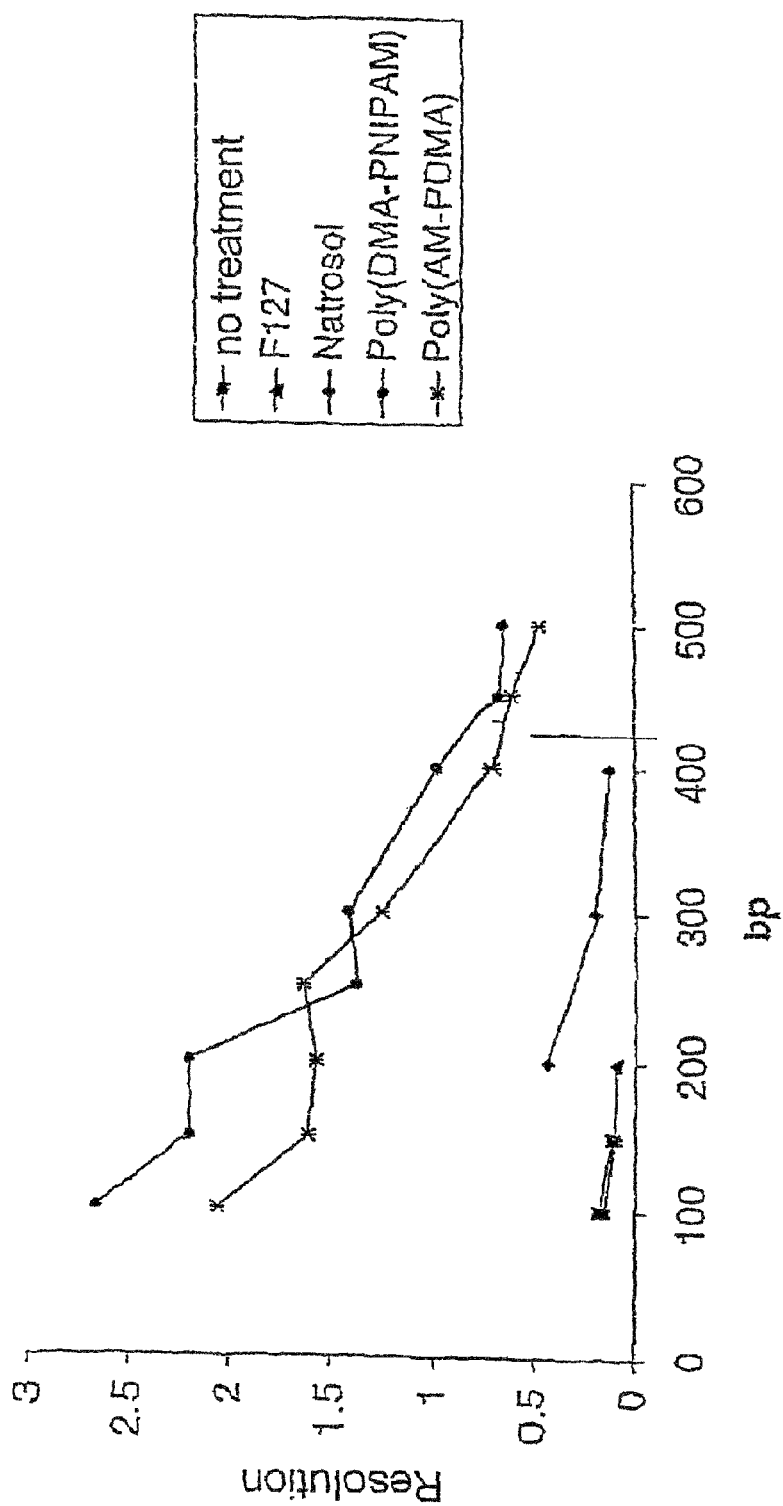

FIG. 14 is a comparison of the calculated resolution between peaks differing by one base to 500 bases, obtained at 50° C. in an ABI 310 device (Perkin-Elmer), using as separation medium a 100 mM Na TAPS buffer containing 2 mM EDTA and 7 M urea, in which 5% of linear acrylamide (molecular mass 700,000-1,000,000) is dissolved, in a capillary initially not treated ("no treatment"), and after pretreatment of the capillary with an aqueous solution containing 3% of the various polymers F127, Natrosol Plus, "PDMA-NIPAM" described in example 9 and PAM-PDMA-1 described in example 11.

Figure 15:
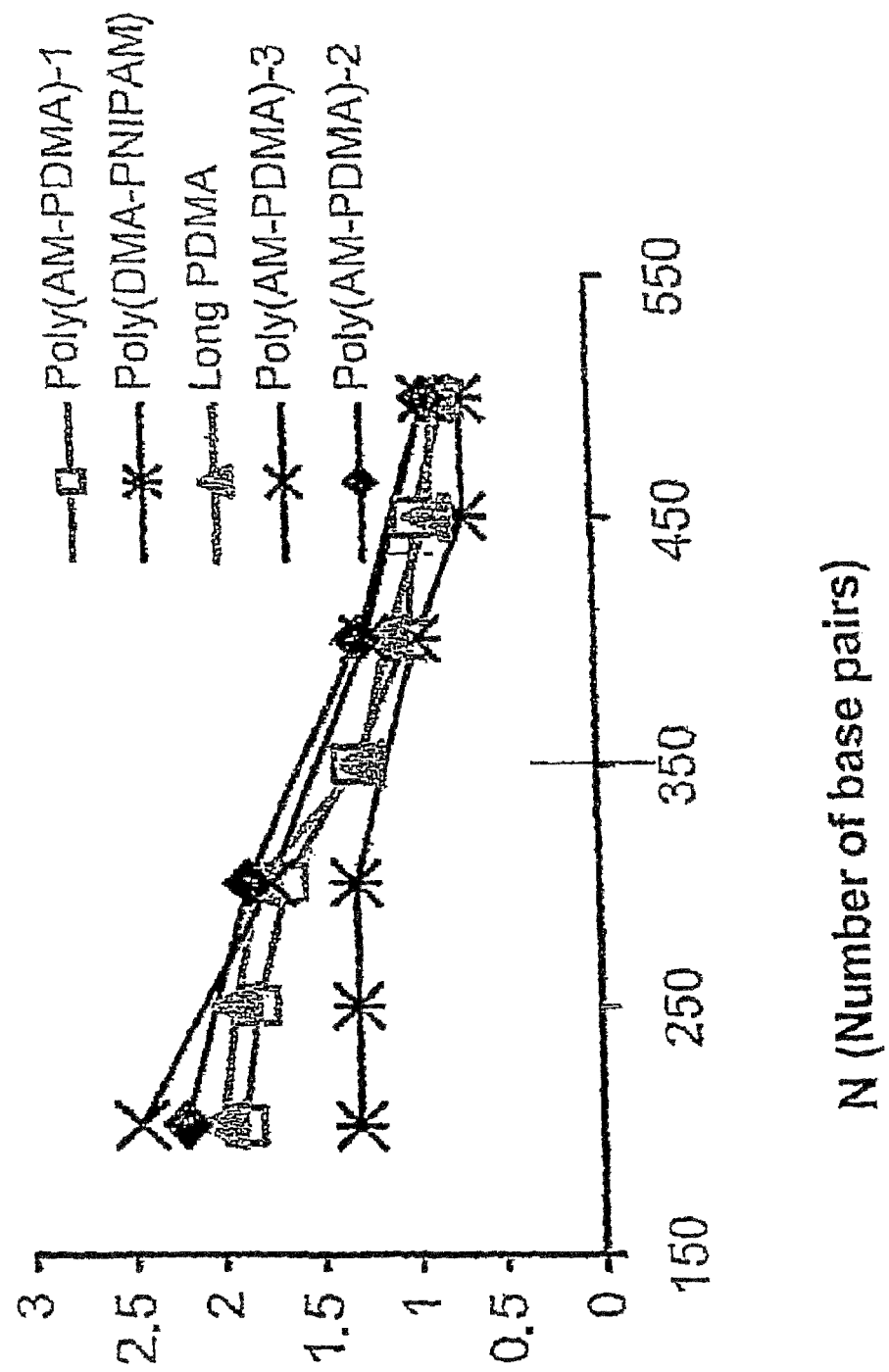

FIG. 15 is a comparison of the resolution according to the number of base pairs for the separation of a "50-500 bp sizer" (Pharmacia-Amersham), in a solution containing 5% of linear polyacrylamide exhibiting no wall treatment properties, in a 2 mM EDTA, 0.1 M Taps, 7 M urea buffer with addition of 0.5% of the following polymers according to the invention: poly(AM-PDMA)-1 (prepared according to example 11), poly(AM-PDMA)-2 (prepared according to example 15), poly(AM-PDMA)-3 (prepared according to example 16), poly(DMA-PNIPAM) (prepared according to example 9), and, by way of comparison, with addition of 0.5% of linear PDMA homopolymer.

DETAILED DESCRIPTION OF THE INVENTION

The present invention more particularly relates to a aqueous liquid medium, for purifying or separating species inside an element comprising walls or for treating the walls of said element, which liquid medium does not display, between its solidification point plus 10° C. and its boiling point minus 10° C., a variation n in viscosity by a factor of 2 or more over a temperature range of 20° C. or less, said medium comprising at least one polymer composed of several polymer segments, wherein said polymer is
   (a) an irregular block polymer, or
   (b) an irregular comb polymer wherein all the segments of a least one type of chemical or topological nature forming part of the composition of said comb polymer have a polydispersity of at least 1.5 and wherein the side branches of said comb polymer have a molecular mass greater than 1500, and wherein said polymer has an average of at least three junction points established between polymer segments of different chemical or topological nature.

For the purposes of the invention, the term "polymer" denotes a product consisting of a set of macromolecules and characterized by certain properties such as molecular mass, polydispersity, chemical composition and microstructure. The "polydispersity" characterizes the molecular mass distribution of the macromolecules, in the meaning of the mass-average familiar to those skilled in the art. The term "microstructure" means the way in which the monomers forming part of the chemical composition of the macromolecules are arranged within the latter.

According to the invention, the term "liquid" means, as opposed to a "gel", any condensed medium capable of flowing, whether it is newtonian or viscoelastic.

In the present case, gels derived from the copolymerization of monomers in the presence of difunctional or multifunctional crosslinking agent(s) are excluded from the field of the invention. The reason for this is that, given their crosslinked state, these gels are solid or elastic and are therefore not liquid. In particular, they are unsuitable for introduction into a capillary.

The liquid medium of the invention in its different applications, including as a solution treatment for the walls of a container or channel, and as a separation medium, is nonthermosensitive, i.e. it does not display, between its solidification point plus 10° C., and its boiling point minus 10° C., a sudden change in its viscosity. The term "sudden change" means a variation by a factor of 2 or more, over a temperature range of 20° C. or less.

For the purposes of the invention, the expression "separation method" is intended to cover any method directed toward separating, purifying, identifying or analyzing all or some of the species contained in a sample. In this case, the liquid is referred to as the "separating medium" and through it pass the species to be separated or at least some of them in the course of the separation process.

The term "species" is generally intended to denote particles, organelles or cells, molecules or macromolecules, and in particular biological macromolecules, for instance nucleic acids (DNA. RNA or oligonucleotides), nucleic acid analogs obtained by synthesis or chemical modification, proteins, polypeptides, glycopeptides and polysaccharides. In analytical methods, said species are commonly referred to as "analytes".

The invention is particularly advantageous in the case of electrokinetic separation methods.

The term "electrokinetic separation" is intended to cover any method directed toward separating all or some of the species contained in a mixture by making them migrate in a medium by the action of an electric field, whether the field exerts its motor action on the analytes directly or indirectly, for example by means of a displacement of the medium itself, for instance in electrochromatography, or by means of a displacement of associated species such as micells, in the case of micellar electrochromatography, or by any combination of direct and indirect actions. Any separation method in which said action of the electric field is combined with another motor action of nonelectric origin are also considered as an electrokinetic separation method according to the invention. Accordingly, methods of capillary electrophoresis or of electrophoresis on "chips" are referred to as "electrokinetic".

Advantageously, in particular in the case of electrokinetic separations, the liquid will consist of an electrolyte.

For the purposes of the invention, the term "electrolyte" denotes a liquid capable of conducting ions. In the most common case, this medium is a buffered aqueous medium, for instance buffers based on phosphate, tris(hydroxymethyl) aminomethane (TRIS), borate, N-tris(hydroxymethyl)methyl-3-aminopropanesulfonic acid (TAPS), histidine, lysine, etc. Numerous examples of buffers that may be used in electrophoresis are known to those skilled in the art, and a certain number of them are described, for example, in Sambrook et al., "Molecular Cloning: a laboratory manual", Cold Spring Harbor Lab, New York, 1989. However, any type of electrolyte may be used in the context of the invention, especially aqueous-organic solvents such as, for example, water-acetonitrile, water-formamide or water-urea mixtures, or polar organic solvents such as, also by way of example, N-methylformamide. The "sequencing buffer" electrolytes consisting of an aqueous buffer at alkaline pH containing an appreciable proportion of urea and/or of formamide are found to be particularly useful in the context of the invention.

The term "channel" denotes any volume delimited by one or more solid walls, having at least two orifices and intended to contain a fluid or to have a fluid pass through it.

The term "crosslinked" is intended to mean, as normally accepted by those skilled in the art, a set of polymers exhibiting between them a large-scale network of crosslinking points, which confers to this set of polymers the properties of a solid or of a gel.

In the present invention, the term "element" is more particularly intended to denote mainly any channel used for the transport, analysis, purification and separation of a fluid or of species contained in this fluid, or any container used to conserve a fluid. Also covered under this definition are solid particles such as beads, for example, liable to be brought into contact with a fluid for the purposes of analysis, separation or purification, in particular by affinity. This definition also extends to any element intended to constitute a wall of a channel or of a container used in an operation of transport, analysis, purification, conservation or separation of a fluid or of species contained in this fluid, or to be part of said wall. The treatment, using such a solution, of the surface of "DNA chips", as described, for example, in "Nature Genetics", 1999, 21, 1-60, of "protein chips", of microtitration plates, or more generally of surfaces intended to be brought into contact with a fluid in a system of analysis or separation, or in a "high throughput screening" system, in particular, falls within the scope of the invention. In the description of the invention, the operation consisting of modifying the properties of the interface between said element and a fluid is indifferently designated by "wall treatment" or "surface treatment".

According to a preferred variant, useful in applications of the invention for the treatment of the surface of elements, the polymer according to the invention has a chemical composition which is different from that of the materials making up said element. It may thus confer to the walls of said channel or of said container advantageous properties which are difficult or impossible to obtain in its absence, given the chemical nature of the elements making up the channel or the container.

Advantageously therefore, the polymers used according to the invention minimize the adsorption of species to the walls and thus improve either the rate of recovery of these species, for example in preparative or micropreparative systems, or the resolution in analytical methods, or else avoid the contamination of said walls, in particular in the transport, analysis or conservation of biological fluids liable to contaminate said walls or elements.

The invention is particularly advantageous in systems comprising at least one channel, at least one dimension of which is submillimetric, such as capillary electrokinetic separation systems, microfluid systems and, more generally, systems for separating species using microchannels, microcontainers or nanocontainers.

According to one preferred variant, the polymers according to the invention exhibit on average at least four junction points, preferably a number of junction points of between 4 and 100 and more preferably a number of junction points of between 4 and 40.

The term "junction point" means a point connecting either two polymer segments of significantly different chemical nature, for instance in the case of a block copolymer, or a point of crosslinking between more than two polymer segments of identical or different chemical nature, for instance in comb polymers. By way of example, a comb polymer bearing three side branches comprises three junction points and seven separate polymer segments. Similarly, a sequential block copolymer of A-B-A-B type comprises three junction points and four separate polymer segments.

For the purposes of the invention, the terms "polymer segment" and "segment" denote a set of monomers linked together in a linear and covalent manner, and belonging to a given type of chemical composition, i.e. having specific overall physicochemical properties, in particular as regards the solvation, the interaction with a solid wall, a specific affinity toward certain molecules, or a combination of these properties.

An example of a polymer segment for the purposes of the invention is given by the sequence, within a copolymer, of monomers that are all identical (homopolymer segment), or a copolymer that has no significant composition correlation over distances of more than a few monomers (segment of random copolymer type).

The polymer according to the invention is composed of several "different" polymer segments. Two polymer segments that differ in their chemical nature and/or their topology, i.e. the spatial distribution of the segments relative to each other, for example skeleton as opposed to side branch, are different for the purposes of the invention.

According to a first preferred variant, the polymers according to the invention are of the irregular block copolymer type.

For the purposes of the invention, the term "block copolymer" denotes a copolymer consisting of several polymer segments linked together covalently, and belonging to at least two different types of chemical composition. Thus, two adjacent polymer segments within a linear block copolymer are necessarily of significantly different chemical nature. The block copolymer is defined by the fact that each of the segments comprises a sufficient number of monomers to have within the separating medium physicochemical properties, and in particular in terms of solvation, that are comparable to those of a homopolymer of the same composition and of the same size. This is in contrast with a random copolymer, in which the various types of monomer follow each other in an essentially random order, and give the chain locally overall properties that are different from those of homopolymers of each of the species under consideration. The size of the homopolymer segments required to obtain this block nature may vary as a function of the types of monomers and of the electrolyte, but it is typically a few tens of atoms along the skeleton of said segment. It should be noted that it is possible to make a block copolymer within the meaning of the invention, in which all or some of the segments themselves consist of a copolymer of random type, insofar as it is possible to distinguish within said block copolymer polymer segments of size and of difference in chemical composition that are sufficient to give rise from one segment to another to a significant variation in the physicochemical properties, and in particular in the solvation. In particular, in order to be considered as a "polymer segment" within the meaning of the invention, a portion of polymer must comprise along its skeleton at least 10 atoms.

According to one preferred mode of this variant, the polymer according to the invention is of the irregular sequential block copolymer type.

For the purposes of the invention, the term "sequential block copolymer" means a block copolymer composed of polymer segments belonging to at least two different chemical types, linked together in a linear manner.

According to a second preferred variant, the polymer according to the invention is of the irregular comb polymer type.

In this case, one preferred variant of an irregular comb polymer consists in displaying segments of at least one type of chemical or topological nature forming part of the composition of said comb polymer having a polydispersity of at least 1.5 and side branches of said comb polymer having a molecular mass greater than 1500.

For the purposes of the invention, the term "comb polymer" denotes a polymer having a linear skeleton of a certain chemical nature, and polymer segments known as "side branches", of identical or different chemical nature, which are also linear but significantly shorter than the skeleton, and are covalently attached to said skeleton via one of their ends. In a comb polymer, the polymer segments constituting the skeleton and those constituting the side branches differ in their topological nature. If the polymer segments constituting the side branches of the comb polymer and those constituting its skeleton also differ in their chemical nature, the polymer simultaneously has the characteristic of a "comb polymer" and that of a "block copolymer". Such polymers, which are known as "comb copolymers", constitute a subset of comb polymers and can, of course, be used in the context of the invention.

Needless to say, the combined use of block copolymer(s) and comb polymer(s) in a medium in accordance with the invention may be envisaged.

The number of polymer segments of a given chemical or topological type present in the polymers according to the invention is understood as being an average value, it being understood that it is always a matter of a population of a large number of molecules having in said numbers a certain polydispersity.

In the present description and unless otherwise mentioned, all the molecular masses and also all the averages for all the chains or all the polymer segments, for instance the average molecular mass, or the average number of atoms along the skeleton, the number of junction points, or the average number of grafts in the case of a comb polymer, are understood as being mass averages within the usual meaning of polymer physics.

All the polymers under consideration according to the invention, namely block copolymers or comb polymers, also have the advantageous characteristic of being of irregular type. According to one aspect of the invention, all the segments of at least one type of chemical or topological nature forming part of their composition have a polydispersity of at least 1.5 and preferably greater than 1.8.

The polydispersity of a type of polymer segment forming part of the composition of a polymer according to the invention is understood as being the average value of the molecular mass of said segments, taken over all the segments of this type forming part of the composition of said polymer (mass average within the usual meaning of polymer physicochemistry).

Another preferred variant of an irregular comb polymer consists in displaying a polydispersity of the segments of the skeleton included between two side branches of at least 1.5 and preferably greater than 1.8.

In another preferred embodiment, the segments of each of the types of chemical or topological nature forming part of the composition of the polymers according to the invention have a polydispersity of at least 1.5 and preferably greater than 1.8.

According to one preferred embodiment, the polydispersity of the polymers according to the invention is greater than 1.5 and preferably greater than 1.8.

The length and number of the different polymer segments present in the comb polymers or the copolymers used in the media according to the invention, and also the chemical nature thereof, may vary significantly in the context of the invention, and the properties of said media may thus be varied widely depending on the desired application, as will be shown more specifically in the description of the implementation examples.

According to one preferred embodiment, at least one segment of the polymer according to the invention is of hydrophilic nature.

According to one preferred embodiment, the polymers according to the invention have a molecular mass (massaverage) greater than 50,000, preferably greater than 300,000, more preferably greater than 1,000,000 and better still greater than 3,000,000.

According to one preferred embodiment, said polymers according to the invention show within the separating medium significant affinity for the walls of said channel.

One particularly preferred mode consists in presenting within the polymer according to the invention at least one type of polymer segment showing, within the separating medium contained in a channel with walls, or within the fluid in which it is carried for the purpose of treating the wall of an element, specific affinity for the wall, and at least one type of polymer segment showing in said medium less or no affinity for the wall.

The presence of polymer segments of this type allows the medium according to the invention to reduce the adsorption of species onto the walls of the channel and/or the electroosmosis.

The polymers according to the invention of the type containing polymer segments of at least one type showing within the separating medium specific affinity for the wall, have, on account of the presence of a plurality of segments of this type, and on account of the relatively high average molecular mass of said segments, a high adsorption energy, and thus reduce the electroosmosis in a long-lasting manner. Moreover, since the polymers according to the invention also comprise in their structure polymer segments that show in said medium less or no affinity for the wall, they avoid an excessively hydrophobic nature that is harmful for resolution, and can more efficiently repel the analytes from the walls.

Typically, types of polymer segments that show no affinity for the wall consist of polymers that show good solubility in the separating medium. However, there may be polymers which are soluble in said medium, but which nevertheless show therein particular affinity for a wall. When the separating medium is an aqueous solution, segments with no affinity for the wall are typically highly hydrophilic segments. On the other hand, segments with affinity are relatively nonhydrophilic, or even hydrophobic. Needless to say, other more specific types of affinity may be used, depending on the nature of the wall and that of the separating medium or that of the fluid in which said polymer is carried for the purpose of treating the wall of an element.

Copolymers that are optimized for performing the invention are especially those in which all the segments that have specific affinity for the wall represent between 2% and 80% by mass and preferably between 5% and 50% or 5% and 30% of the total average molar mass of said copolymers, or between 3% and 85% or 3% and 90% and preferably between 5% and 50%, or 5% and 60% of the total composition of the copolymers in terms of number of moles of monomers.

Another preferred embodiment, which is particularly advantageous when the analytes are biological macromolecules, consists in using polymers according to the invention that also show specific affinity for one or more analytes.

This affinity may be obtained by incorporating into the structure of said polymers polymer segments capable of showing specific affinity for certain analytes. Such polymer segments may consist, for example, and in a nonexhaustive manner, of a predetermined sequence of different monomers, for instance a polynucleotide or a polypeptide. This affinity may also be obtained by combining with the polymer according to the invention a native or denatured protein, a protein fraction or a protein complex, or alternatively an acidic or basic function, and/or a function of Lewis acid or Lewis base type.

According to another embodiment, particularly useful for surface treatments, the copolymers which are optimized for use of the invention are in particular those in which all of the segments exhibiting a particular affinity with the wall represent between 2 and 25% by mass, preferably between 5 and 15%, of the average total molar mass of said copolymers, or between 3 and 30%, and preferably between 5 and 20% of the total composition of the copolymers in number of moles of monomers.

As illustrations of the various structures that may be adopted by the copolymer according to the invention, mention may be made most particularly of those in which all or some of said copolymer is:
  in the form of irregular sequential block copolymers. In this case, one preferred variant consists in alternating, along the polymer, segments with specific affinity for the wall, and segments with reduced or no affinity for the wall. It may also be envisaged to alternate, along the polymer, segments showing specific affinity for certain analytes, and segments showing reduced or no affinity for said analytes;
  in the form of irregular comb copolymers. In this case, one preferred variant is characterized in that said polymers are in the form of comb polymers whose skeleton consists of several polymer segments that show specific affinity with the wall, and the side branches of which consist of polymer segments showing reduced or no affinity for the wall, or comb polymers whose side branches consist of polymer segments showing specific affinity for the wall, and whose skeleton consists of polymer segments showing reduced or no affinity for the wall. These polymers may also be in the form of comb polymers, certain side branches of which consist of polymer segments showing specific affinity for certain analytes, and the skeleton of which consists of polymer segments showing reduced or no affinity for these analytes.

Needless to say, systems in which several types of preferred variants above are combined together, either by combining polymer segments of more than two different types, or in the form of a mixture of different copolymers, also fall within the scope of the invention. It is thus possible, for example, to combine within a copolymer according to the invention polymer segments showing affinity for the wall, polymer segments or groups showing specific affinity for certain analytes, and polymer segments showing no specific affinity either for the walls or for the analytes. It is also possible, again by way of example, to combine in a medium according to the invention block copolymers comprising polymer segments showing affinity for the wall and polymer segments showing no specific affinity either for the walls or for the analytes, and polymers comprising polymer segments or groups showing specific affinity for certain analytes, and polymer segments showing no specific affinity either for the walls or for the analytes.

In one preferred mode of the invention, all of the polymer segments of a given type of chemical or topological nature have on average along their skeleton a number of atoms of greater than 75, and more preferably greater than 210, or have a molecular mass of greater than 1,500 and preferably greater than 4,500.

According to an even more preferred embodiment, the various types of segments have along their skeleton an average number of atoms of greater than 75, and more preferably greater than 210, or have a molecular mass of greater than 1,500 and preferably greater than 4,500.

According to one preferred embodiment, the invention also relates to a separating medium consisting in a liquid in which at least one polymer in accordance with the invention is dissolved to a proportion of from 0.1% to 20% and preferably from 1% to 6% by weight. It is particularly advantageous, for implementing the invention, to use block copolymers or comb homopolymers in which at least one of the types of segments consists of a polymer chosen from polyethers, polyesters, for instance polyglycolic acid, soluble random homopolymers and copolymers of the polyoxyalkylene type, for instance polyoxypropylene, polyoxybutylene or polyoxyethylene, polysaccharides, polyvinyl alcohol, polyvinylpyrrolidone, polyurethanes, polyamides, polysulfonamides, polysulfoxides, polyoxazoline, polystyrene sulfonate, and substituted or unsubstituted acrylamide, methacrylamide and allyl polymers and copolymers.

As representatives of the types of polymer segments showing, in an aqueous separating medium, little or no affinity with the walls, mention may be made most particularly of polyacrylamide and polyacrylic acid, polyacryloylaminopropanol, water-soluble acrylic and allylic polymers and copolymers, dextran, polyethylene glycol, polysaccharides and various cellulose derivatives such as hydroxyethylcellulose, methylcellulose, hydroxypropylcellulose, hydroxypropylmethylcellulose or methylcellulose, polyvinyl alcohol, polyurethanes, polyamides, polysulfonamides, polysulfoxides, polyoxazoline, polystyrene sulfonate, and also polymers bearing hydroxyl groups, and all the random copolymers of the derivatives mentioned above.

Needless to say, other polymer segments that are soluble in the separating medium may be used according to the invention, as a function of the nature of said fluid and of that of the walls of the channel, the particular application and the ease of introducing them into a block polymer of the desired structure.

As representatives of the polymer segments, which may or may not be soluble in aqueous solvents, and which may show therein particular affinity for the walls, mention may be made of dimethylacrylamide, acrylamides N-substituted with alkyl functions, acrylamides N,N-disubstituted with alkyl functions, allyl glycidyl ether, copolymers of the above acrylic derivatives with each other or with other acrylic derivatives, alkanes, fluoro derivatives, silanes, fluorosilanes, polyvinyl alcohol, polymers and copolymers involving oxazoline derivatives, and also in general polymers that have a combination of carbon-carbon bonds, ether-oxide functions and epoxide functions, and also all the random copolymers of these compounds.

Many types of polymer segments may be chosen to make up the polymer segments constituting a polymer according to the invention, as a function of the envisaged electrolyte, from all the types of polymers known to those skilled in the art, in particular from those soluble in aqueous medium. Reference may thus be made to the book "Polymer Handbook" Brandrupt & Immergut, John Wiley, New York.

Another preferred embodiment, which is particularly advantageous when the species to be separated are biological macromolecules, consists in using copolymers according to the invention which also exhibit a different affinity with different analytes.

This affinity may be obtained by integrating into the structure of said polymers segments capable of exhibiting an affinity specific for certain species to be separated. Such segments may, in a nonexhaustive manner, consist, for example, of a predetermined sequence of different monomers, such as a polynucleotide or polypeptide. This affinity may also be obtained by associating with the polymer according to the invention a native or denatured protein, a protein fraction or a protein complex, or alternatively an acid or basic function and/or a function such as an acid or base in the Lewis sense.

According to this variant, it is possible to envision either alternating along a linear block copolymer segments exhibiting a specific affinity with certain analytes and segments exhibiting less or zero affinity with said analytes, or introducing into a comb copolymer polymer segments exhibiting an affinity specific for certain analytes, either in the form of additional side branches or of subsidiary segments in their backbone.

The polymers according to the invention may be natural or synthetic. According to one preferred variant for the variety and control that it allows with regard to the microstructure, the polymers according to the invention are synthetic polymers.

The following are most particularly suitable for the invention:
- copolymers of the comb copolymer type, the skeleton of which is of dextran, acrylamide, acrylic acid, acryloylaminoethanol or (N,N)-dimethylacrylamide type and onto which are grafted side segments of acrylamide, substituted acrylamide or (N,N)-dimethylacrylamide (DMA) type, or of the DMA/allyl glycidyl ether (AGE) copolymer type, or alternatively of homopolymer or copolymer of oxazoline or of oxazoline derivatives;
- non-thermosensitive copolymers of the irregular sequential block copolymer type having along their skeleton an alternation of segments of polyoxyethylene type and of segments of polyoxypropylene type, or an alternation of segments of polyoxyethylene type and of segments of polyoxybutylene type, or more generally an alternation of segments of polyethylene and of segments of polyether type that are appreciably more hydrophobic than polyoxyethylene;
- copolymers of the irregular sequential block copolymer type having along their skeleton an alternation of segments of acrylamide, acrylic acid, acryloylaminoethanol or dimethylacrylamide type, on the one hand, and segments of (N,N)-dimethylacrylamide (DMA) type, or of DMA/allyl glycidyl ether (AGE) copolymer type, or alternatively of homopolymer or copolymer of oxazoline or of oxazoline derivatives;
- polymers of the irregular comb polymer type, the skeleton of which is of agarose, acrylamide, substituted acrylamide, acrylic acid, acryloylaminoethanol, dimethylacrylamide (DMA), or allyl glycidyl ether (AGE) polymer type, of DMA/AGE random copolymer type, of oxazoline and oxazoline derivative, of dextran, of methylcellulose, of hydroxyethylcellulose, of modified cellulose, of polysaccharide or of ether oxide type, and onto which are grafted side segments of agarose, acrylamide, substituted acrylamide, acrylic acid, acryloylaminoethanol, dimethylacrylamide (DMA), or allyl glycidyl ether (AGE) polymer type, of DMA/AGE random copolymer type, of oxazoline and oxazoline derivative, of dextran, of methylcellulose, of hydroxyethylcellulose, of modified cellulose, of polysaccharide or of ether oxide type;
- copolymers of the irregular comb copolymer type, the skeleton of which is of the acrylamide, substituted acrylamide, acrylic acid, acryloylaminoethanol, dimethylacrylamide (DMA), or allyl glycidyl ether (AGE) polymer type, of DMA/AGE random copolymer type, of oxazoline and oxazoline derivative, of dextran, of agarose, of methylcellulose, of hydroxyethylcellulose, of modified cellulose, of polysaccharide or of ether oxide type, and bears short-chain hydrophobic side segments such as alkyl chains, aromatic derivatives, fluoroalkyls, silanes or fluorosilanes.

It should also be noted that, in most applications, it is preferable to use a polymer according to the invention that is essentially neutral. However, it may be useful for certain applications, and in particular to avoid the adsorption of species containing both charges and hydrophobic portions, to select a polymer according to the invention that is deliberately charged, preferably opposite in charge to that of said species.

The copolymers according to the invention are advantageous because of their ability to combine properties belonging to polymers which are chemically different in nature, which cannot always be brought together in a homopolymer or a random copolymer. Thus, they allow more flexible adaptation of the chemical nature of the copolymer, as a function, firstly, of the chemical nature of the fluid and, secondly, of the chemical nature of the wall of the channels or containers. They are thus particularly advantageous in applications using channels or containers consisting of polymers or elastomers such as PDMS (polydimethylsiloxane), PMMA poly(methyl methacrylate), polycarbonate, polyethylene, polypropylene, polyethylene terephthalate, polyimide, polycyclohexane, polyurethanes or organic materials such as ordinary glass, borosilicate glass. Pyrex, molten silica, silicon oxide, ceramics, silicon, diamond, zirconium or semiconductors. Moreover, the polymers according to the invention have the unique property of being able to have, on each polymer, a considerable number of polymer segments exhibiting a significant affinity with the wall, which allows a large energy of absorption, and therefore a long-lasting reduction of electroosmosis, while at the same time also containing a considerable number of loops not exhibiting affinity with the walls, which may serve to avoid the adsorption of the species.

As regards the preparation of the copolymers used according to the invention, it may be carried out by any conventional polymerization or copolymerization technique. The choice of preparation method is generally made by taking into account the structure desired for the copolymer, i.e. comb or linear structure, and the chemical nature of the various blocks of which it is made.

As representatives of these preparation variants, mention may be made most particularly of processes according to which said copolymers are obtained by:

polycondensation, ionic or free-radical polymerization or copolymerization of identical or different monomers, of identical or different macromonomers, or of a mixture of identical or different monomers and macromonomers, or by grafting several polymer segments onto a linear or branched polymer skeleton of identical or different chemical nature.

Preferably, all or some of the copolymers used according to the invention are obtained by a: copolymerization of monomers and macromonomers comprising a reactive function at at least one of their ends, or b: copolymerization of macromonomers comprising at least one reactive function in their structure.

For the purposes of the invention, the term "reactive function" means a group that allows the molecule bearing this group to be incorporated into the macromolecule during the copolymerization reaction without interrupting said copolymerization.

With the aid of the rules and preferred modes listed above, a person skilled in the art is capable of preparing the copolymers in accordance with the invention, by adapting the structure, the nature and the mode of preparation of said polymers as a function of the desired separation properties for one application or another.

A subject of the present invention is also a process for separating, analyzing and/or identifying species contained in a sample, characterized by performing the following steps:

a/ filling the channel of a separating device with separating medium according to the invention, b/ introducing said sample containing said species into one end of said channel, c/ applying an external field intended to move certain species contained in the sample, especially an electric field, and d/ recovering or detecting the passage of said species at a point along the channel that is different from the point of introduction of the sample.

In one preferred variant, it is not necessary to change the temperature between the capillary filling stage and the analysis stage.

Depending on the particular applications, the separating medium may contain, besides the polymers according to the invention, other elements, and in particular components that interact with the species or the walls. Many elements of this type are known to those skilled in the art.

In the present case, it is possible to combine in the separating medium polymers of the irregular block copolymer type, and other polymers capable of interacting with analytes either by steric interaction or by affinity, in order to improve the performance qualities compared with those obtained with the polymer according to the invention used alone. In this case, polymers that are more particularly preferred according to the invention are those having a mass fraction of polymer segments showing specific affinity for the wall that is greater than when these polymers are used alone. This fraction may be between 20% and 80%.

A subject of the present invention is also the use of a separating medium according to the invention for separating, purifying, filtering or analyzing species chosen from molecular or macromolecular species, and in particular biological macromolecules, for instance nucleic acids (DNA, RNA or oligonucleotides), nucleic acid analogs obtained by synthesis or chemical modification, proteins, polypeptides, glycopeptides and polysaccharides, organic molecules, synthetic macromolecules or particles such as mineral particles, latices, cells or organelles.

In the case of electrophoresis analysis methods, the invention is particularly useful for DNA sequencing, for which it allows minimum bandwidths to be obtained. It is also particularly favorable for separating proteins, proteoglycans, or cells, for which the problems of adsorption onto the wall area particular handicap and particularly difficult to solve.

According to one aspect of the invention, the separation or analyzing of species of the process according to the invention involves discrimination of said species by affinity or molecular hybridization.

Advantageously, the claimed medium may be used in a channel of which at least one dimension is of submillimetric size.

As regards the apparatus, the claimed medium is particularly advantageous for microfluidic systems, since it makes it possible, by means of an optimum choice of the various types of blocks within the polymers, to combine blocks that show good affinity for the surface of the channel in order to obtain a long-lasting treatment, and blocks that show good repulsion for the species to be separated, irrespective of said species and of the chemical nature of said channel.

The media according to the invention and the separation methods using these media are particularly advantageous for electrophoretic separation and diagnostic applications, gene typing, and high-throughput screening, quality control, or for detecting the presence of genetically modified organisms or pathogens in a product, or detecting the presence of dangerous material in an object or device.

In point of fact, the polymers of which the separating medium under consideration in the context of the present invention is composed are found to be advantageous in several respects.

Firstly, their capacity to display "block polymer" nature allows them to combine properties belonging to polymers of different chemical nature, and that cannot always be united in a homopolymer or a random copolymer. They thus make it possible to more flexibly adapt the chemical nature of the separating medium, firstly as a function of the species to be separated, and secondly as a function of the chemical nature of the channels in which the separation is performed. They are thus particularly advantageous both in applications using channels consisting of polymers or elastomers such as PDMS (polydimethylsiloxane), PMMA (polymethyl methyacrylate), polycarbonate, polyethylene, polypropylene, polyethylene terephthalate or polyimide, or of mineral materials such as glass, ceramics, silicon, stainless steel or titanium, and in more traditional applications using channels whose walls are made of fused silica.

Compared with the block copolymers of the prior art, the polymers according to the invention also show superior performance qualities in terms of resolution, which is most probably associated with their irregular nature, i.e. the polydispersity of the polymer segments forming part of the polymers according to the invention. This characteristic is particularly surprising, since the set of block copolymers used in the prior art deliberately involves copolymers containing regularly spaced segments and/or having a selected and essentially uniform length (i.e. low polydispersity). This polydispersity of the segments, in the polymers according to the invention, also shows advantages in terms of cost and flexibility in formulating, since polymers comprising such polymolecular segments are not only more efficient, but also easier to prepare. In particular, they may be prepared with high molecular masses.

In the applications for which a reduction of electroosmosis or interaction of species with the wall is desired, the polymers according to the invention have, on account of the presence in their structure of a large number of polymer segments that show significant affinity for the wall, high adsorption energy and can thus reduce the electroosmosis and the adsorption of species in a long-lasting manner.

Finally, it is also very likely that the combination of a linear skeleton and of a plurality of junction points gives the separating media according to the invention some of the properties of gels at the local scale, which is beneficial in terms of separation efficiency, while at the same time conserving them at the large scale, and in particular as regards the flow properties, properties that are comparable with those of linear polymers.

Depending on the applications, the chemical nature of the capillary for which the surface treatment solution according to the invention, also called medium for treating the walls of the channel, is intended and the particular choice of polymer according to the invention used for the treatment, said solution may comprise, as a basis for dissolving the copolymers according to the invention, an aqueous (preferably buffered) solution, an organic solvent, an aqueous-organic solvent or an electrolyte.

In a preferred variant, the polymers contained in the surface treatment solutions according to the invention attach to the solid walls or surfaces thanks to at least physical adsorption without establishing a covalent bond.

According to another preferred variant, the polymers contained in the surface treatment solutions according to the invention attach to the solid walls or surfaces thanks to at least one or more covalent bonds.

Using the preferred rules and modes stated above, those skilled in the art are capable of preparing polymers in accordance with the invention, by adapting the structure, the nature and the method of preparation of said polymers as a function of the desired properties for one application or another.

A subject of the invention is also a process for treating the surface of an element, in particular to avoid the phenomena of electroosmosis and/or of nonspecific adsorption of species capable of manifesting themselves at this surface when it is brought into contact with a fluid, and/or of species contained in this fluid.

More precisely, it is a process for treating the surface of an element intended to be brought into contact with a fluid and/or species contained in this fluid during the transport, analysis, purification, separation and/or conservation of said fluid, comprising bringing said element into contact with at least one noncrosslinked polymer of the block copolymer or comb polymer type, having on average at least three junction points between polymer segments chemically or topologically different in nature and more particularly bringing said element into contact with at least one medium according to the invention.

According to one aspect of the present invention, the fluid is a biological fluid, a fluid containing or liable to be contaminated with organic or biological products, or a fluid containing or liable to be contaminated with live organisms.

For the definition of the polymer and of the element, reference will be made to the preceding description.

According to a preferred variant of the invention in its surface treatment aspect, the polymer is used in the form of an aqueous solution of polymer as claimed and preferably containing said polymer at a concentration of between 0.01% and 20%, and more preferentially between 0.1 and 5% by mass.

According to a first embodiment, the process comprises treating the element, prior to its use, with a treatment solution in accordance with the invention.

When the treatment is carried out for the purpose of a transport or conservation operation, this solution has a composition different from that of the fluid intended to be transported or conserved. When the treatment is carried out for the purpose of a separation application, this solution has a composition different from that of the separation medium. The treatment is obtained by leaving said solution in contact with the walls for the necessary period of time. Depending on the application and the embodiment, this period of time may be very variable, ranging from a fraction of a second to several hours, or even, for the most difficult applications, several days. This solution is then removed from the channel or container, prior to or simultaneously with the filling thereof with said fluid. According to this variant, said fluid does not, itself, contain the polymers according to the invention. Thus, the latter remain present in the channel or the container only in a form adsorbed to the walls, and do not contribute to modifying the properties of said fluid. In particular, they do not significantly increase its viscosity. Depending on the application, this treatment may be renewed between each transport or separation operation, or, on the other hand, after a given number of separations or else when a degradation of the properties is noted, making it necessary.

According to a preferred variant of the invention, the bringing of said surface treatment solution into contact with the surface of the element with respect to which a reduction of the nonspecific adsorption or the electroosmosis is desired may be followed by a treatment intended to reinforce the action of said solution, such as, by way of nonlimiting example, thermal treatment, treatment by radiation (light radiation, ultraviolet radiation, X rays, gamma rays, etc.), drying of the wall, or incubation thereof in the presence of a liquid different from said solution.

However, this treatment is not always necessary, and some polymers according to the invention which are part of the composition of the surface treatment solutions of the invention are capable of effectively minimizing the nonspecific adsorption and the electroosmosis without subsequent treatment.

According to a preferred embodiment, in particular if many separations are carried out between two surface treatments with a solution according to the invention, the surface of the element may be "regenerated" before the treatment, with a solution intended to clean off the wall the impurities adsorbed in the course of the separations. Such treatments are known to those skilled in the art and may advantageously comprise washing with an acid solution, with an alkaline solution, with a solution of detergent, with an organic solvent, or with a combination of these methods.

According to a second embodiment, the process claimed comprises the addition of said polymer to the fluid which must be transported, analyzed, purified, separated and/or conserved.

According to this second embodiment, the copolymers which characterize the surface treatment solutions according to the invention are preferably introduced directly into the fluid transported, conserved or used as a separation medium, at a concentration sufficiently low so as not to significantly modify, moreover, the other customary properties of said fluid, and in particular without increasing its viscosity more than 2-fold, relative to the same fluid in the absence of said polymers. According to an even more preferred variant, the polymers according to the invention do not modify the viscosity of said fluid more than 1.5-fold.

As regards the fluid into which the polymer according to the invention is directly introduced, it may advantageously contain, besides the polymers according to the invention, other elements, and in particular components which interact with the species either by steric interaction or by affinity, and which are capable of inducing between one another a total or partial separation of these species. Many components of this type, such as hydrophilic linear polymers, micelles, surfactants or chiral compounds are known to those skilled in the art.

Of course, the present invention extends to any process of separation, filtration, analysis and/or purification involving the use of the claimed process. These processes of filtration, separation, analysis and/or purification are partly identified below.

The present invention also relates to an element, preferably channel, container or particles, or any element intended to constitute a wall of a channel or of a container used in an operation of transport, analysis, purification, conservation or separation of a fluid or of species contained in this fluid, or intended to form part of said wall, treated with the surface treatment solution claimed.

Such elements may be used for the separation, purification, filtration or analysis of species chosen from molecular or macromolecular species, and in particular biological macromolecules such as nucleic acids (DNA. RNA, oligonucleotides), nucleic acid analogs obtained by chemical modification or synthesis, proteins, polypeptides, glycopeptides and polysaccharides, organic molecules, synthetic macromolecules or particles such as mineral particles, latex particles, cells or organelles.

The elements treated according to the invention are also of particular use for DNA sequencing insofar as they make it possible to obtain minimum bandwidths. Similarly, they are found to be suitable for separating proteins, proteoglycans or cells, for which it is known that problems of adsorption to the wall are particularly bothersome and particularly difficult to solve.

However, the possibility offered by the invention of greatly varying the chemical nature of the surface is also advantageous for other applications.

The surface treatment solutions according to the invention, the processes using these solutions and, more particularly, the elements treated according to the invention are of use for diagnostic, genotyping, high-throughput screening and quality control applications, or for detecting the presence of genetically modified organisms or pathogens in a product, or detecting the presence of dangerous material in an object or device.

The invention is also particularly advantageous for "hybridization" or "affinity" techniques in which the intention is to analyze or separate, within a channel or a container, the species contained in a sample, as a function of their respective specific affinity for ligands. These ligands are either contained in said channel or container, or are attached at predetermined positions on the walls of said container or said channel. The invention makes it possible to carry out this type of analysis, while at the same time avoiding or minimizing the nonspecific adsorption of said species to the walls of the channel or of the container, or to solid surfaces contained in said channel or in said container.

According to a preferred embodiment, this type of ligand may be associated with the element, namely channel, container, element forming part of the composition of said channel or container, or particles, via a treatment with a surface treatment solution according to the invention. In this instance, the treatment solution according to the invention performs two functions. It reduces the nonspecific adsorption and provides said ligands or contributes to immobilizing them at the level of said element.

A family of polymers which is particularly advantageous for applications of analysis by affinity consists of a block copolymer simultaneously having 1/ a multiplicity of polymer segments exhibiting an affinity specific for a wall of the channel or of the container, or certain predetermined parts of said walls, or else with certain solid surfaces present in said channel or of said container, such as the surfaces of particles or latex beads, and 2/ one or more polymer segments not exhibiting affinity with said walls or surfaces, and bearing ligands specific to certain species, the analysis of which is desired. Said ligands may in particular be oligonucleotides, proteins, antibodies, peptides or, more generally, biological or synthetic polymers or polymer fragments.

The advantage of the invention in this application is that it keeps the ligands linked to said walls or surfaces indirectly, while at the same time maintaining said ligands at a considerable distance from the latter. Specifically, in the context of the invention, the polymer segment(s) bearing the ligands do not exhibit any affinity for the wall and are therefore pushed away from it by the steric interactions. The polymers according to the invention therefore enable the analytes to interact with the ligands, without approaching the walls.

A subject of the present invention is also the use of the claimed solution for minimizing the phenomena of adsorption or of electroosmosis which occur at the surface(s) of an element intended to be brought into contact with a fluid and/or species contained in this fluid during the transport, analysis, purification, separation or conservation of said fluid.

The invention is particularly advantageous for the transport, analysis or conservation of a biological fluid containing or liable to be contaminated with inorganic, organic or biological products or live organisms.

As regards the devices, the surface treatment solutions, the process and the components claimed are of particular use for microfluid systems, microtitration plates, "DNA chips and protein chips" and, more generally, all systems of transport and analysis involving high surface/volume ratios, since they make it possible, through the optimal choice of the various types of block within the polymers, to combine blocks exhibiting good affinity for the surface of the walls in order to obtain a long-lasting treatment, and blocks exhibiting good repulsion for the species to be separated, whatever said species may be and whatever the chemical nature of said component.

The following Examples are nonlimiting illustrations of the present invention. Examples 1 to 7 are concerned with the liquid separating medium aspect present invention. Examples 8 to 17 are concerned with the surface treatment solution aspect of the invention.

Example 1

Preparation of a Functionalized PDMA Macromonomer with a Molecular Mass in the Region of 10,000, for the Preparation of Copolymers in Accordance with the Invention Polymerization of PDMA The free-radical polymerization of N,N-dimethylacrylamide (DMA) is performed in pure water. The initiator is a redox couple for which the oxidizing agent is potassium persulfate K2S2O2 (KPS) and the reducing agent is aminoethanethiol AET.HCl. The initiation reaction is:

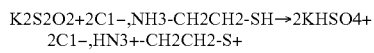
K2S2O2+2Cl−,NH3-CH2CH2-SH→2KHSO4+ 2Cl−,HN3+-CH2CH2-S+

AET.HCl also acts as transfer agent, which allows the chain length to be controlled.

Procedure 0.18 mol of DMA and 200 ml of water are placed in a 500 ml three-necked flask on which is mounted a condenser, and equipped with a nitrogen inlet device. The mixture is then stirred and heated to 29° C. with a water bath. Sparging with nitrogen is commenced. After 45 minutes, 0.61 g of AET.HCl (0.0054 mol) predissolved in 20 ml of water is added, followed by addition of 0.0018 mol of potassium persulfate (KPS) dissolved in a minimum amount of water. The mixture is stirred for 3 hours. The solution is then concentrated and then freeze-dried.

To isolate the polymer, a precipitation is performed according to the following procedure:

The solid obtained is redissolved in 100 ml of methanol. The hydrochloride present is neutralized by adding 0.0054 mol of KOH (i.e. 0.30 g dissolved in about 25 ml of methanol) incorporated dropwise into the solution. The salt formed. KCl, precipitates and is extracted by filtration. The filtrate thus recovered is concentrated and then poured dropwise into 4 liters of ether. The precipitated polymer is recovered by filtration through a No. 4 sinter funnel. The solid is then dried under vane-pump vacuum. The mass yield is about 50%.

The above protocol leads to an amino polymer known as "PDMA" and corresponds to initiator/monomer ratios Ro=0.03 and Ao=0.01, in which:

2) Modification of the Amino PDMA

The PNIPAM macromolecules synthesized contain amine functions at the chain ends, these chains originating from the initiator aminoethanethiol AET.HCl.

By reaction of the amine function with acrylic acid, a vinyl double bond is attached to the chain end according to the following reaction scheme:

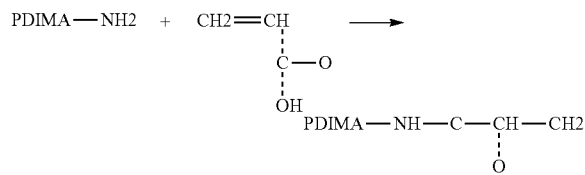

Procedure:

50 ml of methylene chloride, 1.5 g of acrylic acid (0.021 mol), 9 g of PDMA and 4.3 g of dicyclohexylcarbodiimide (DCCI) (0.021 mol) are placed in a 100 ml beaker.

The reaction medium is stirred for one hour. Since the acrylic acid is in large excess relative to the PDMA (the amount of acrylic acid is about twenty times that of the PDMA), all the amino functions have been modified. The mixture is then filtered through a No. 4 sinter funnel to remove the precipitated dicyclohexylurea, the by-product resulting from the conversion of the DCCI. The purification is performed by precipitation from ether.

A macromonomer PDMA-1 bearing an allyl function at the chain end is thus obtained with a mass yield of about 70%.

The average molar mass and the polydispersity of the macromonomers thus prepared, measured by SEC (steric exclusion chromatography), are of the order of 15,000 and 2, respectively.

Example 2

Preparation of a Copolymer PCAN-PDMA)-1 with an Acrylamide Skeleton and PDMA Grafts, of Molecular Mass 1,500 kdalton The copolymerization of amino PDMA (0.4 g) and of acrylamide (2.8 g) is performed for 4 hours in 50 ml of water at room temperature, while degassing vigorously with argon. The initiator used is the redox couple of ammonium persulfate ((NH4)2S2O8) [0.075 mol % of the amount of monomers]/sodium metabisulfite (Na2S2O5) (0.0225 mol % of the amount of monomers). The resulting copolymer is purified by precipitation from acetone and dried under vacuum. Its molecular mass is 1,500 kdalton, and its polydispersity Mw/Mn is about 2. The degree of incorporation of macromonomer, measured by proton NMR, is about 6%, which corresponds to an average number of side branches on the skeleton of about 6.

On account of the free-radical polymerization method used, the macromonomers constituting the side chains are incorporated into the polymer chain at random positions determined by chance by the collisions between molecules (random distribution). This polymerization method leads to a distribution of the molecular masses of the polymer segments of the skeleton between two side branches of approximately exponential shape, and thus to polydispersities of said polymer segments of the skeleton that are largely superior to 1.8.

Example 3

Figure 1A:
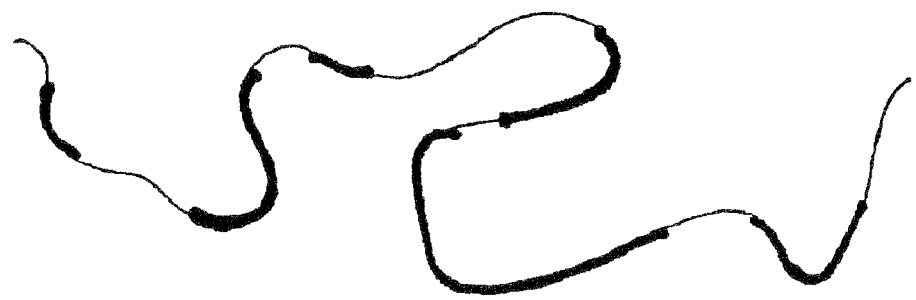
FIGS. 1a, 1b, and 1c are examples of diagrammatic configurations for an irregular sequential block copolymer (1a), an irregular comb polymer (1b), and an irregular comb copolymer (1c). The bold lines correspond to one type of chemical nature, and the fine lines to another type of chemical nature.
Figure 1B:
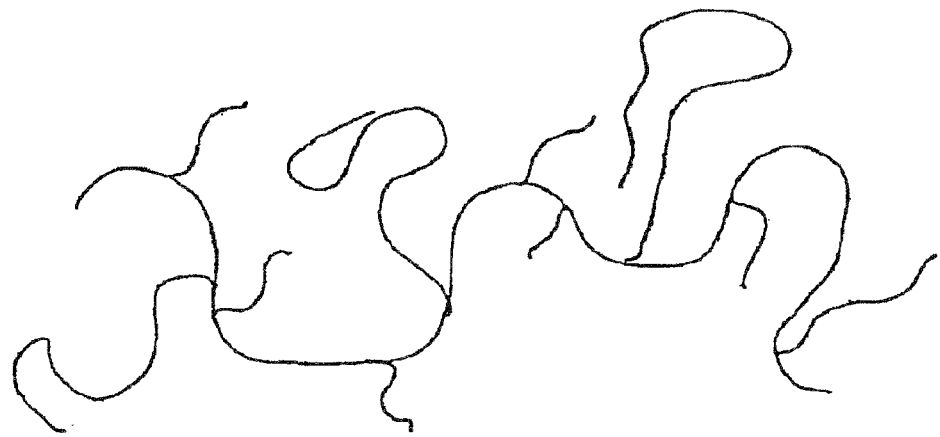
Figure 1C:
Figure 2:
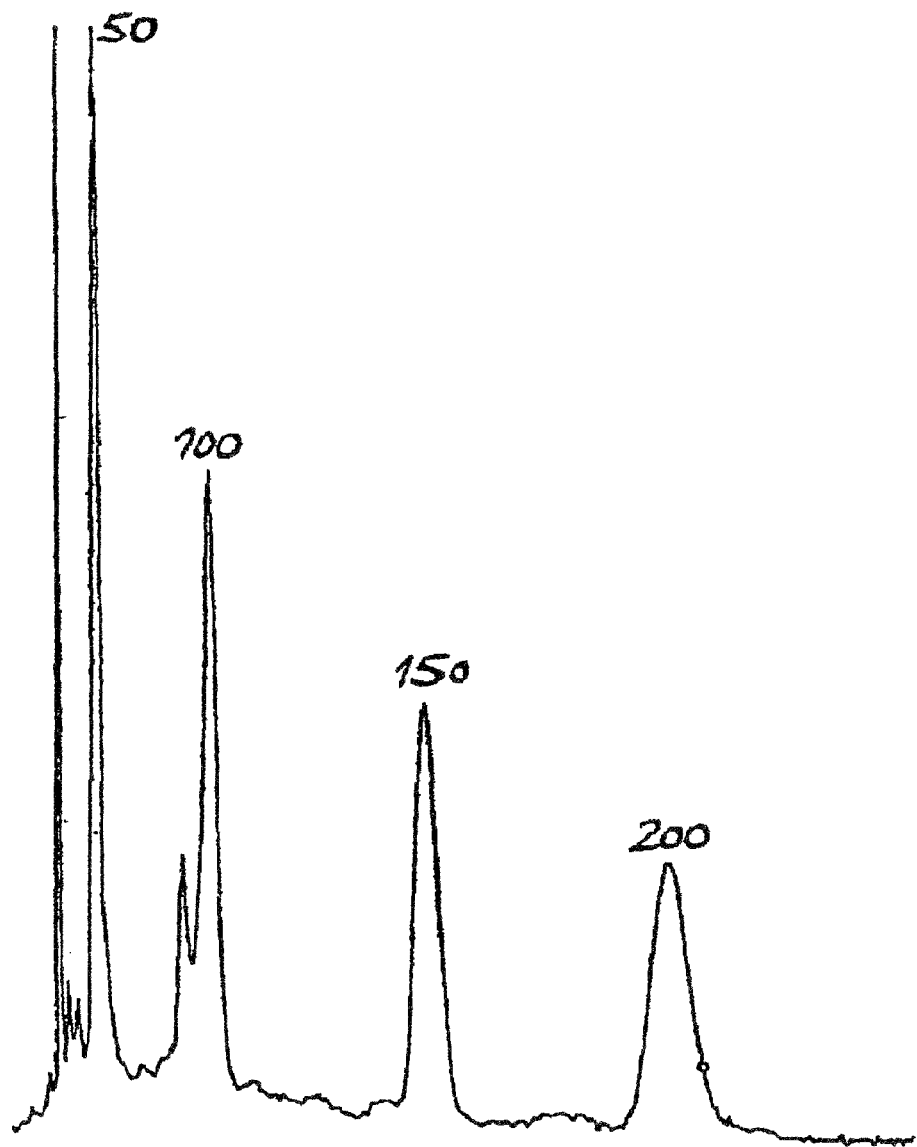
FIG. 2 is a control electrophoregram representing the separation of the Pharmacia Biotech 50-500 bp sizer, obtained at 50° C. in an ABI 310 machine (Perkin Elmer), using an untreated capillary and, as separating medium, a 100 mM Na TAPS, 2 mM EDTA, 7M urea buffer, in which is dissolved 5% of a commercial homopolymer of the polyacrylamide type (molecular mass 700,000-1,000,000) the DNA sizes corresponding to the various peaks are indicated on the diagram, as number of bases.
Figure 3:
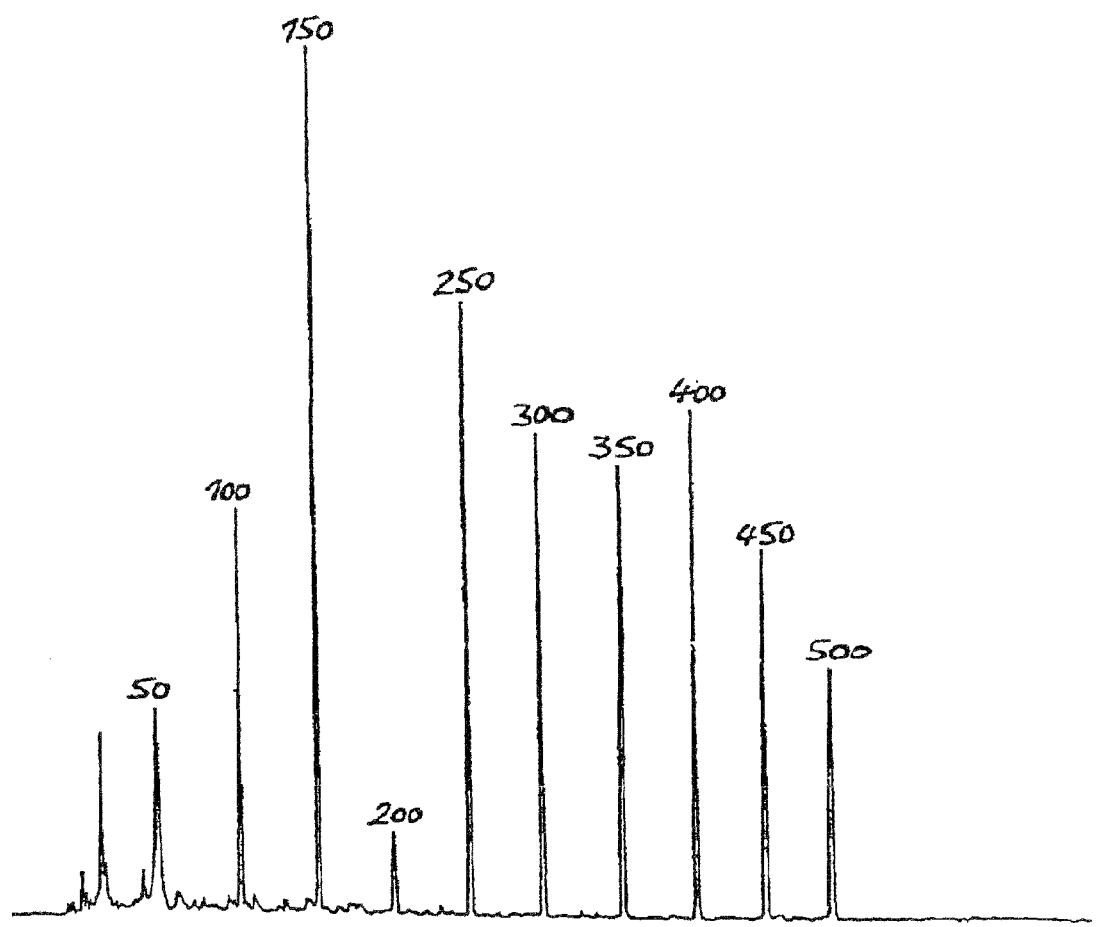
FIG. 3 is a control electrophoregram representing a separation under conditions identical to those of FIG. 2, with a "POP6" commercial separating medium from PE Biosystems. The DNA sizes corresponding to the various peaks are indicated on the diagram, as number of bases.
Figure 4:
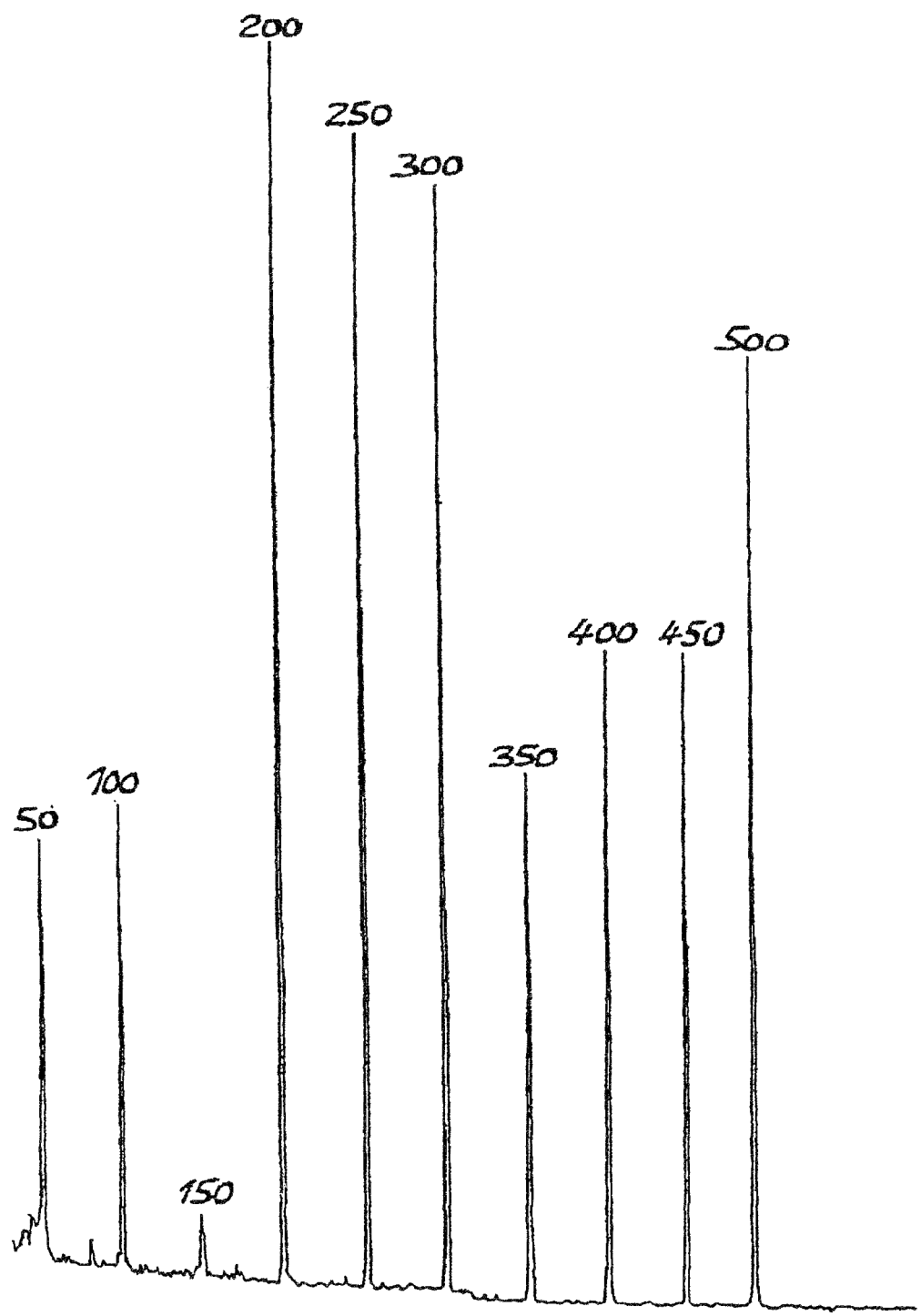
FIG. 4 is an electrophoregram representing a separation under conditions identical to those of FIG. 2, with a 100 mM Na TAPS, 2 mM EDTA, 7M urea separating medium, in which is dissolved 5% of P(AM-PDMA)-2 comb copolymer described in Example 2. The DNA sizes corresponding to the various peaks are indicated on the diagram, as number of bases.
Figure 5:
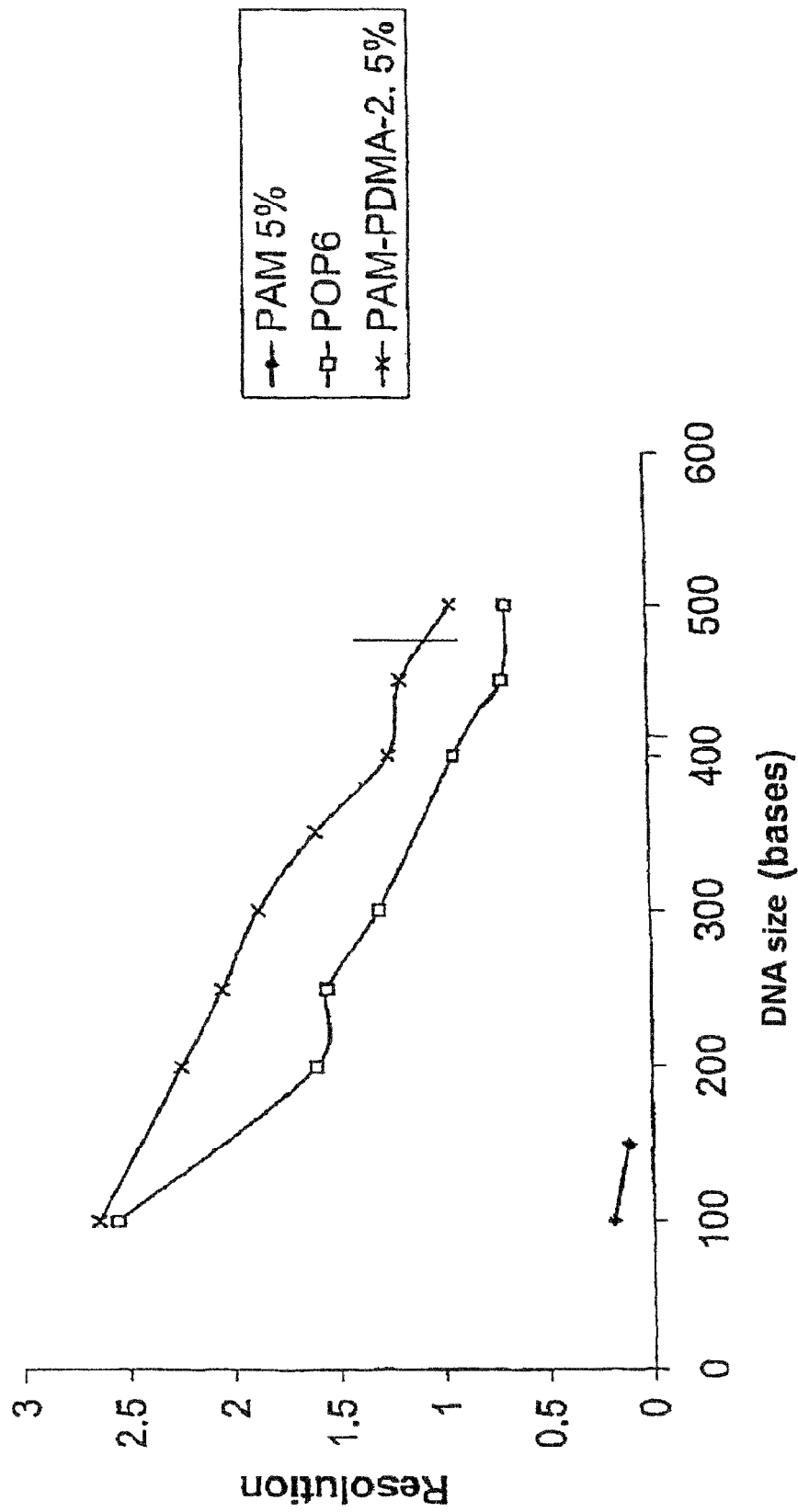
FIG. 5 is a comparison of the resolution calculated between peaks differing from one base to 500 bases, obtained at 50° C. in an ABI 310 machine (Perkin-Elmer), using as separating medium:
  a: a "Pop6" commercial separating medium from PE Biosystems,
  b: a 50 mM Na TAPS, 2 mM EDTA, 7M urea buffer, in which is dissolved 5% of linear acrylamide (molecular mass 700,000-1,000,000)
  c: the same buffer, in which is dissolved 5% of irregular block copolymer according to the invention P(A14-PDMA)-2 described in Example 2.

Separation properties obtained for single-stranded DNA (50-500 bp sizer, Pharmacia Biotech) at 50° C. in an ABI 310 machine (Perkin-Elmer), in a 100 mM Na TAPS, 2 mM EDTA, 7 M urea buffer, in various separation media. It is observed visually (FIG. 4) and more quantitatively by means of the resolution measurements (FIG. 5), that the separating medium according to the invention P(AM-PDMA)-2 improves the resolution relative to the same polymer skeleton not bearing side branches (PAM. FIGS. 2 and 5), but also relative to a commercial product based on linear PDMA (POP6, FIGS. 3 and 5). The separation time is also reduced, which is an additional advantage of the media according to the invention. It thus appears, surprisingly but beneficially, that this polymer according to the invention which comprises a large fraction of acrylamide, and a smaller fraction of PDMA, has, on account of the particular arrangement of said fractions and of the presence of junction points that characterize the invention, properties that are superior to those of each of said components in homopolymer form.

Example 4

Figure 6:
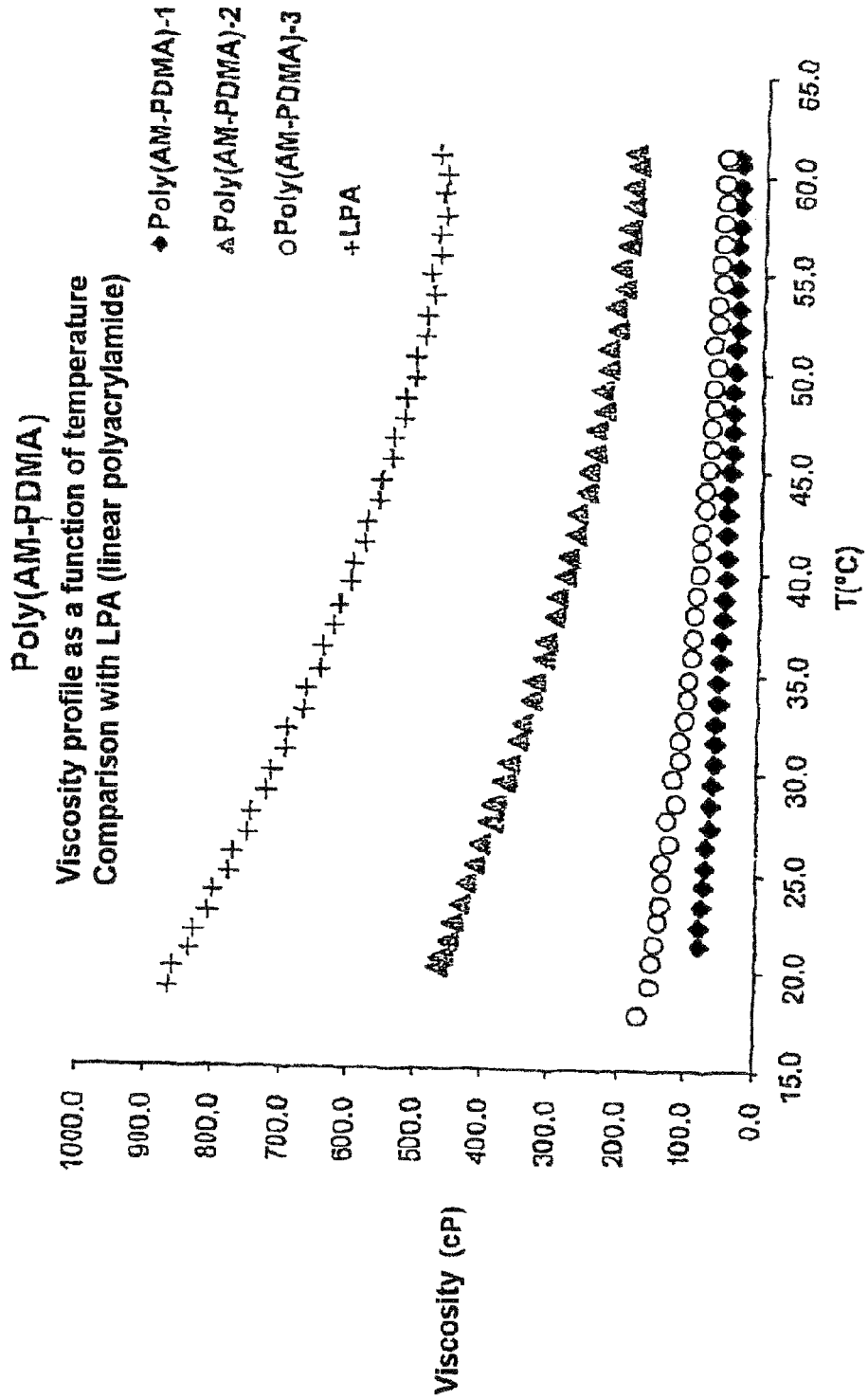
FIG. 6 represents the viscosity of solutions at 3% of linear acrylamide (LPA) and of the copolymers according to the invention poly(AN-PDMA)-1, prepared according to Example 2, poly(AM-PDMA)-2, prepared according to Example 4, and poly(AN-PDMA)-3, prepared according to Example 5.

Preparation of a Copolymer P(AM-PDMA)-2 Containing an Acrylamide Skeleton and PDMA Grafts, of Molecular Mass about 3,000 kdalton The preparation is identical to that described in 30 example 2, except for the concentration of ((NH4)2S2O8) [0.1 mol % instead of 0.075 mol % of the amount of monomers] and of (Na2S2O5) (0.015 mol % instead of 0.0225 mol % of the amount of monomers). The viscosity, presented in FIG. 6, makes it possible to evaluate the molecular mass, of about 3,000 kdalton, starting from that of the p(AM-PDMA)-1, using the cubic dependence of the viscosity as a function of the molecular mass for interlocked polymers.

Example 5

Preparation of a Copolymer P(AM-PDMA)-3 Bearing PDMA Grafts, of Molecular Mass about 30,000

In a first stage, the macromonomer of molecular mass 530,000 is prepared as described in example 1, with the exception of the ratio Ro, which is set at 0.015 instead of 0.03. This macromonomer is then polymerized with acrylamide, according to the protocol described in example 4.

Example 6

Measurement of the viscosity of 3% solutions obtained with the polymers described in examples 2, 4 and 5, and also with a linear acrylamide homopolymer. In this example, each of the polymers was introduced at a rate of 3 g/100 ml into purified water (MilliQ). The viscosity of each of the corresponding solutions was measured on a Brookfield DV3 coneplate rheometer run by the Rheocalc software (Sodexim, Muizon, F). The shear rate selected is 10 (1/s) for a temperature gradient of 1° C. per minute. It is observed in FIG. 6 that the copolymers according to the invention have no thermosensitive nature (their viscosity shows a small and uniform decrease with temperature), and a moderate viscosity. It is also observed that the structure and properties of the copolymers can be varied by controlling the polymerization conditions.

Example 7

Figure 7:
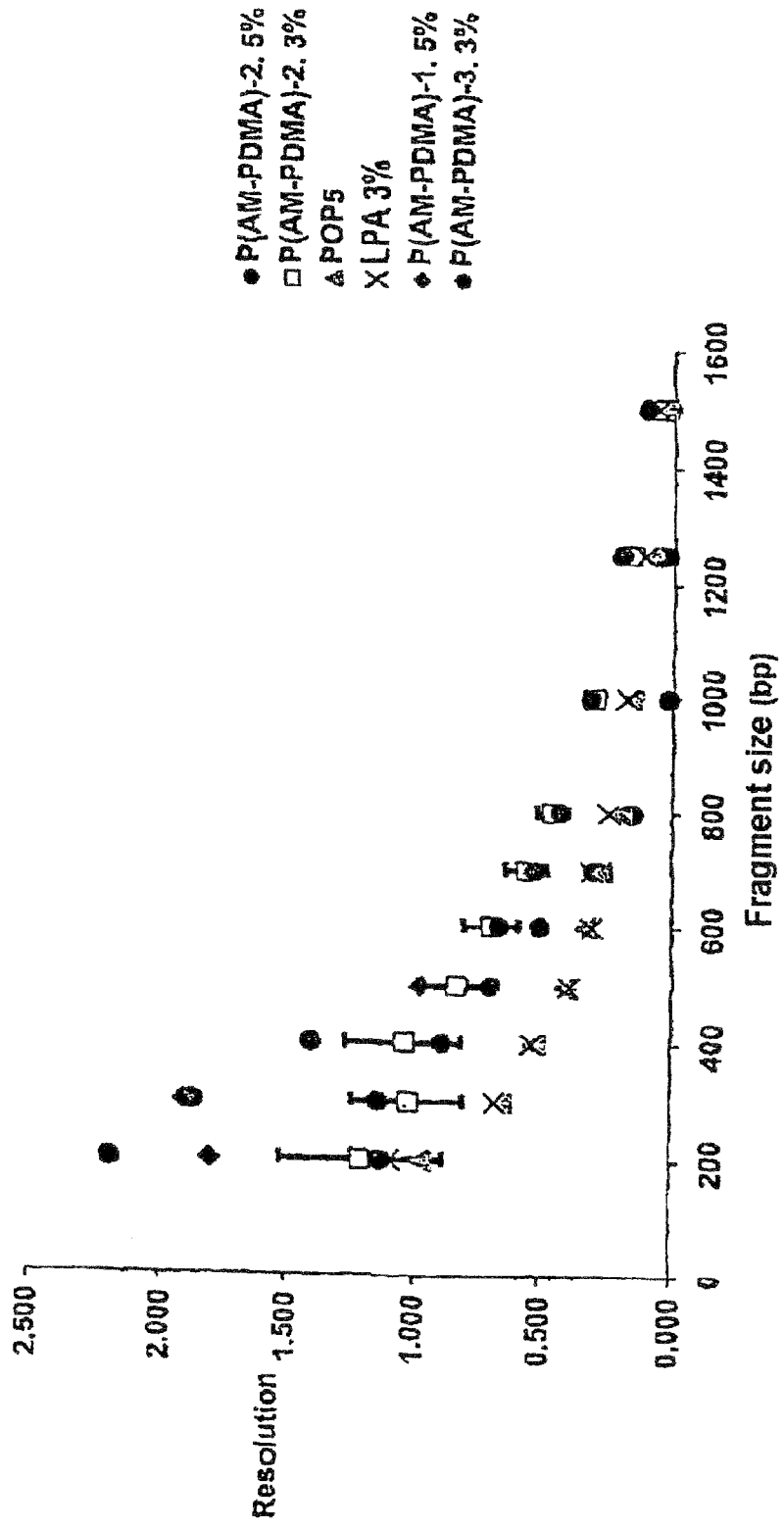
FIG. 7 represents resolutions obtained during the electrophoretic separation of DNA, in solutions of linear acrylamide (LPA), of commercial polymer (POP5), and of the copolymers according to the invention poly(AM-PDMA)-1, prepared according to Example 2, poly(AM-PDMA)-2, prepared according to Example 4, and poly(AM-PDMA)-3, prepared according to Example 5, at 3% and 5%.

Electrophoretic separations of single-stranded DNA fragments, in separating media according to the invention based on copolymers described in examples 2, 4 and 5, and, for comparative purposes, in linear polyacrylamide (LPA) and the commercial separating medium "POP5" (Applied Biosystems). The separation conditions are identical to those of example 4, with the exception of the sample, a "sizer" of 100 to 1,500 bases (BioVentures, USA). It is observed in FIG. 7 that in the range that is most advantageous for sequencing (fragment size 600 to 1,000), the media based on copolymers according to the invention, in particular those corresponding to a mass concentration in the separating medium of 3%, lead to a resolution that is markedly superior to that obtained with the polymers of the prior art. Considering that a resolution of the order of 0.3 to 0.5 is sufficient to sequence DNA to within one base, the media according to the invention should allow reading lengths of greater than 800 bases.

Example 8

Preparation of a Functionalized PNIPAM Macromonomer of Average Molecular Mass in the Region of 10,000 for the Purpose of Preparing Copolymers in Accordance with the Invention 1) Polymerization of the NIPAM The radical polymerization of the NIPAM is carried out in pure water. The initiator is a redox couple in which the oxidant is potassium persulfate, $K_2S_2O_8$ (KPS), and the reducing agent is aminoethanethiol (AET),HCl. The initiating reaction is:

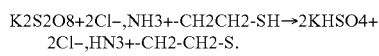

The AET,HCl also plays the role of a transfer agent, which makes it possible to control the length of the chains.

Procedure 20 g of NIPAM (0.18 mol) and 200 ml of water are introduced into a 500 ml three-necked flask surmounted by a cooling apparatus and equipped with a nitrogen inlet device. The mixture is then stirred and heated to 29° C. with a water bath. The sparging of nitrogen is begun. After 45 minutes, 0.602 g of AET,HCl (0.0054 mol) dissolved beforehand in 20 ml of water are added, followed by 0.478 g of potassium persulfate (KPS) dissolved in a minimum amount of water. The mixture is maintained with stirring for 3 hours. Next, the solution is concentrated and than lyophilized.

To isolate the polymer a precipitation is performed according to the following procedure:

The solid obtained is redissolved in 100 ml of methanol. The hydrochloride present is neutralized by adding 0.0054 mol of KOH (i.e. 0.302 g dissolved in approximately 25 ml of methanol) incorporated dropwise in the solution. The salt formed, KCl, precipitates and is extracted by filtration. The filtrate thus recovered is concentrated and then poured dropwise into 4 liters of ether. The polymer precipitates and is recovered by filtration over sintered glass No. 4. The solid is then dried under vacuum by a vane pump. The mass yield is of the order of 50%.

The above protocol produces an aminated polymer name "PNIPAM-A-C", and corresponds to initiator-monomer ratios Ro=0.03 and Ao=0.01, where:

Ro=[R—SH]/[NIPAM] and Ao=[KPS]/[NIPAM].

2) Modification of the aminated PNIPAM, PNIPAM-A-C

The PNIPAM macromolecules synthesized have amine functional groups at the end of the chains, these functional groups originating from the initiator aminoethanethiol, AET, HCl.

By reacting the amine functional group on acrylic acid, a vinyl double bond is attached to the end of the chain according to the following reaction scheme:

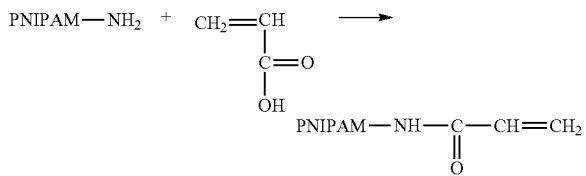

Procedure:

50 ml of methylene chloride, 1.5 g of acrylic acid (0.021 mol), 9 g of PNIPAM and 4.3 g of dicyclohexylcarbodiimide (DCCI) (0.021 mol) are introduced into a 100 ml beaker.

The reaction medium is stirred for one hour. Since the acrylic acid is in great excess relative to the PNIPAM (the amount of acrylic acid is approximately twenty times that of the PNIPAM), all of the amino functional groups were modified. The mixture is then filtered over sintered glass No. 4 in order to remove the dicyclohexylurea precipitate, a byproduct resulting from the transformation of the DCCI.

The mixture is then concentrated down to 15 ml and then transferred dropwise into 200 ml of ether in order to precipitate the polymer. The mixture is filtered over sintered glass No. 4 and the solid is washed with three times 100 ml of ether and then dried under vacuum by the vane pump overnight.

A macromonomer PNIPAM-C bearing an allyl functional group at the end of the chain is thus obtained, with a mass yield of the order of 70%.

The molar masses of the macromonomers thus prepared were measured by SEC (steric exclusion chromatography) in THF at 40° C., with an ultrastyragel column, refractometric double detection and universal calibration with respect to polystyrene samples. NB: I have simplified here.

Other macromonomers (NIPAM) were prepared according to this protocol. They are listed in table I below and are characterized in terms of polydispersity and molecular weight for each of the two types of segment and by weight.

These results show that it is possible to vary the average molecular mass of the macromonomers by varying the temperature of polymerization and the initiator/polymer ratio Ro, the highest Ro ratios leading to the lowest molecular masses. They also show that the polydispersities of the macromonomers are high, in general greater than 2.

TABLE 1

| Molecular mass | PNIPAM-C | PNIPAM-5 | PNIPAM-M | PNIPAM-10 | PNIPAM-L | PNIPAM-20 |
|---|---|---|---|---|---|---|
| Preparation conditions | Ro = 0.03 23° C. | Ro = 0.025 23° C. | Ro = 0.02 25° C. | Ro = 0.02 29° C. | Ro = 0.015 25° C. | Ro = 0.01 25° C. |
| Mw (g/mol) | 10,800 | 12,800 | 15,800 | 20,400 | 23,000 | 34,000 |
| Average number of atoms along the chain | 200 | 230 | 290 | 370 | 420 | 620 |
| Polydispersity (Mw/Mn) | 5.7 | 2.0 | 4.2 | 3.2 | 4.9 | 5 |

Example 9

Preparation of a PDMA-NIPAM copolymer with a comb structure and comprising the PNIPAM-C prepared in example 8, as segments devoid of significant affinity with the wall, and poly(N,N-dimethylacrylamide) (PDMA) as backbone showing an affinity with the wall.

The copolymerization of the PNIPAM-C (0.7 g) and of the DMA (2.8 g) is carried out for 4 h in 30 ml of water at ambient temperature, with vigorous degassing with argon. The initiator used is the redox couple ammonium persulfate (($NH_4$)$_2$$SO_2O_8$) (0.1 mol % of the amount of monomers)-sodium metabisulfite ($Na_2S_2O_5$) (0.03 mol % of the amount of monomers). The resulting copolymer is purified by ultrafiltration in a "Minitan Millipore®", equipped with a membrane having a cutoff of 30,000, and then lyophilized. The final level of incorporation of PNIPAM 10, measured by proton NMR on the polymers diluted to 2 g/100 ml in heavy water (Bruker devices at 250 MHz) is 6.5%. The molecular mass, measured in water at 25° C. by steric exclusion chromatography on a "Shodex®" column with refractometric double detection and two-angle light scattering (Precision Detector), is Mw=3,000,000, and the polydispersity is 2. The average number of side branches along the backbone is deduced from these values and from the molecular mass of the PNIPAM-C, and is of the order of 18.

Due to the method of radical polymerization used, the macromonomers constituting the side chains are integrated into the polymer chain at random positions determined by the chance of collisions between molecules (statistical distribution). This method of polymerization leads to the form of the distribution of the molecular masses of the polymer segments of the backbone between two side branches being approximately exponential, and therefore to the polydispersities of said polymer segments of the backbone being largely greater than 1.8.

Example 10

Preparation of a macromonomer of the PDMA type bearing an acrylic functional group at one end: the reaction is carried out according to the same protocol as example 8, replacing one mole of NIPAM with one mole of DMA. The purification is carried out by precipitation from ether and then filtration.

Example 11

Preparation of Copolymer "PAM-PDMA-1", Having an Acrylamide Backbone which does not Interact with the Wall and pDMA Grafts Exhibiting Strong Affinity with Silica Walls The copolymerization of the pDMA macromonomers prepared in example 10 (0.7 g) and of acrylamide (2.8 g) is carried out for 4 h in 30 ml of water at ambient temperature, with vigorous degassing with argon. The initiator used is the redox couple ammonium persulfate (($NH_4$)$_2S_2O_8$) (0.1% of the amount of monomers)-sodium metabisulfite ($Na_2S_2O_5$) (0.03 mol % of the amount of monomers). The resulting copolymer is purified by ultrafiltration in a "Minitan Millipore®", equipped with a membrane having a cutoff of 30,000, and then lyophilized. The molecular mass, measured by exclusion chromatography (conditions identical to example 9), is Mw=813 kDa, and the polydispersity is 2.2. The mass proportion of pDMA, measured by NMR, is 6.5%, which corresponds on average to 5 side branches along the backbone. As in example 9, the method of radical polymerization used leads to a high polydispersity of the polymer segments of the backbone between two side branches.

Example 12

Figure 8:
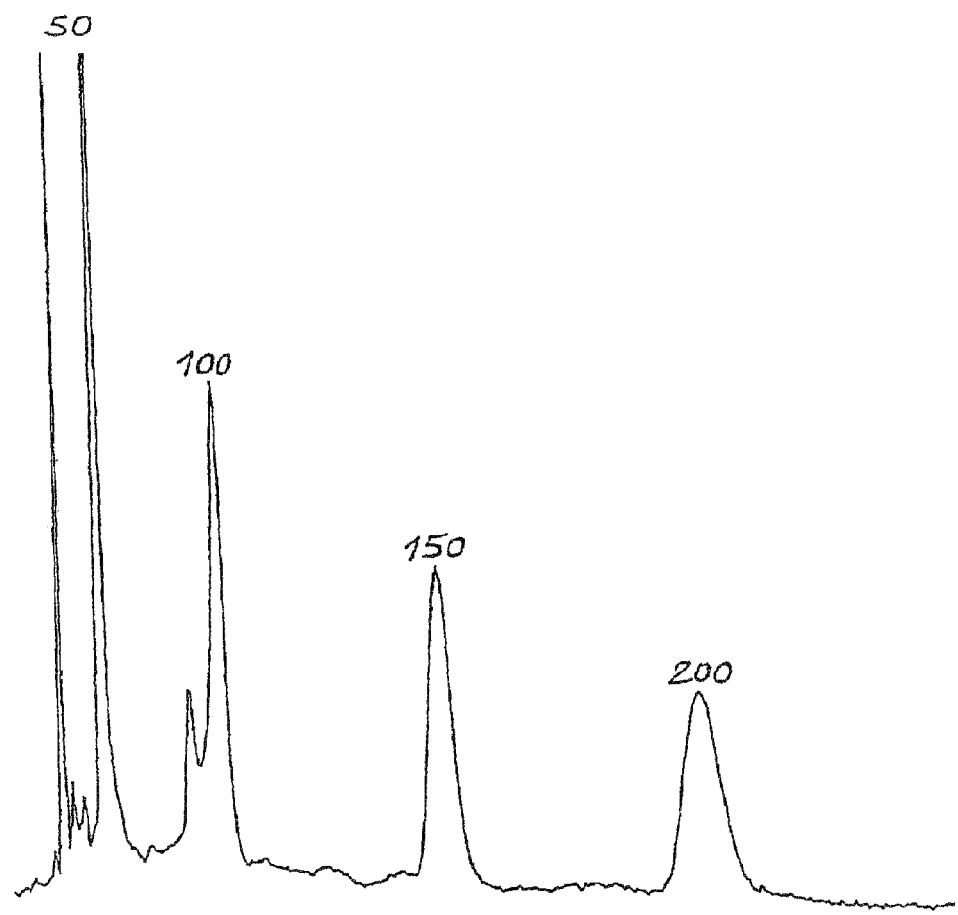
FIG. 8 is a control electropherogram representing the separation of the 50-500 bp sizer. Pharmacia biotech, obtained at 50° C. in an ABI 310 device (Perkin-Elmer), using as separation medium a 100 mM Na TAPS buffer containing 2 mM EDTA and 7 M urea, in which 5% by weight of linear acrylamide (molecular mass 700,000-1,000,000) is dissolved, in a nontreated capillary. The numbers above the peaks indicate the size of the corresponding DNA fragment.
Figure 11:
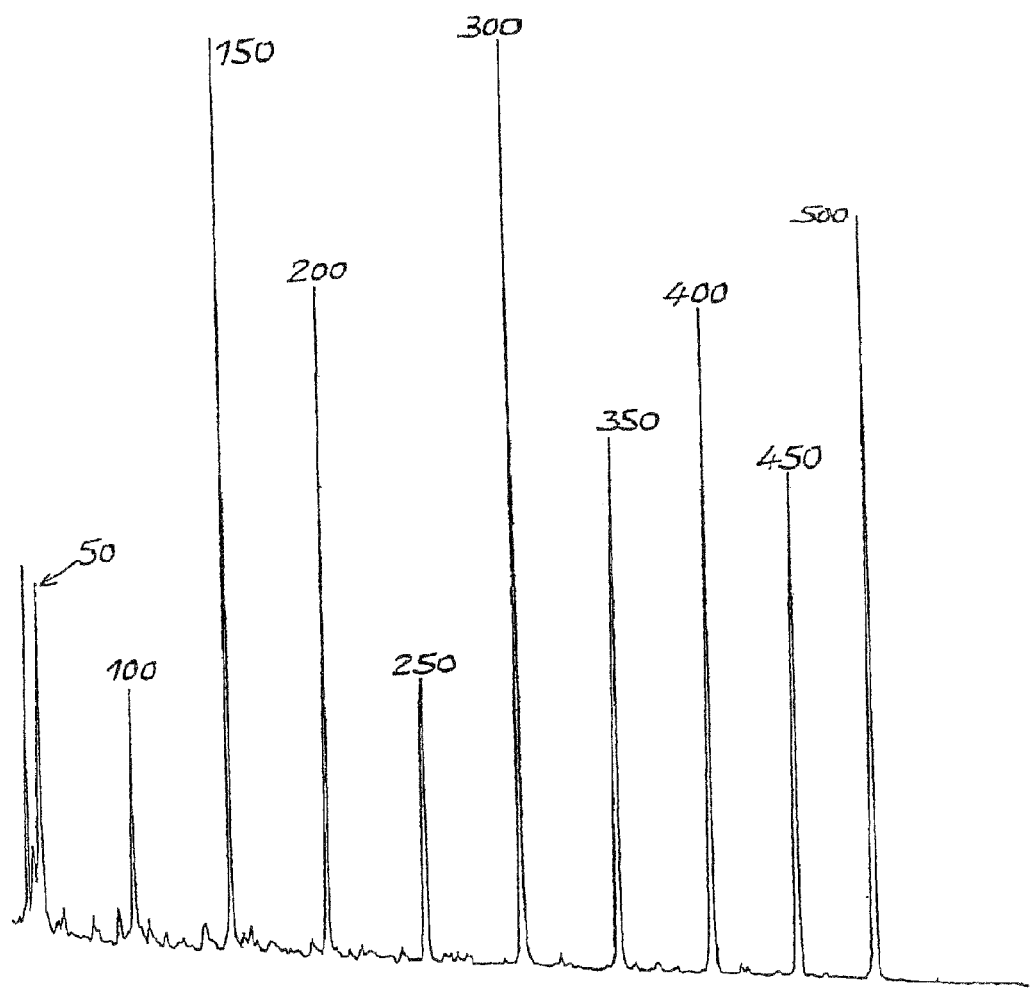
FIG. 11 is an electropherogram representing a separation identical to that of FIG. 8, in a capillary pretreated for 2 hours min with an aqueous solution containing 3% of the copolymer according to the invention "PDMA-NIPAM" described in example 2. The numbers above the peaks indicate the size of the corresponding DNA fragment.
Figure 12:
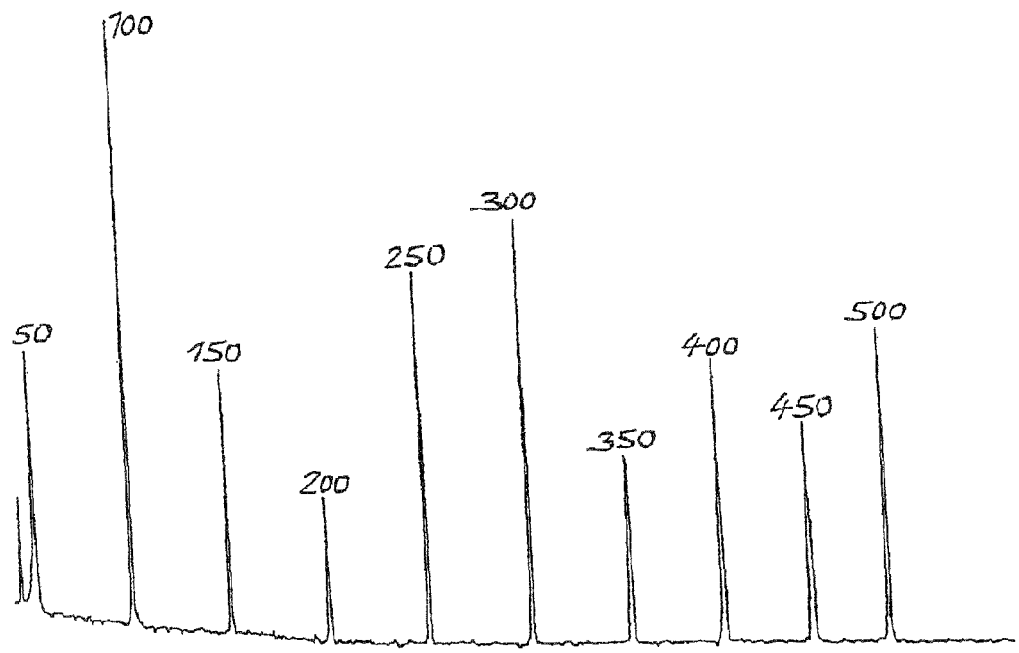
FIG. 12 is an electropherogram representing a separation identical to that of FIG. 8, in a nontreated capillary, with copolymer according to the invention "PDMA-NIPAM" described in example 9 being added to the separation medium at a concentration by mass of 0.5%. The numbers above the peaks indicate the size of the corresponding DNA fragment.

Separation properties obtained for DNA (50-500 bp sizer. Pharmacia biotech), with and without treatment of the silica capillary with the copolymers prepared according to example 9:

The electropherograms are obtained at 50° C. in an ABI 310® device (Perkin-Elmer), in a 50 mM Na TAPS buffer containing 2 mM EDTA and 7 m urea,
  a) in acrylamide without pretreatment of the capillary (FIG. 8)
  b) in acrylamide after treatment of the capillary with a commercial triblock copolymer "pluronics F127", BASF (FIG. 9)
  c) in acrylamide after treatment of the capillary with a commercial comb copolymer having a hydroxyethylcellulose backbone bearing short-chain alkyl functional groups (Natrosol Plus 331, Aqualon) (FIG. 10)
  d) in acrylamide after treatment with the copolymer PDMA-NIPAM prepared according to example 9 (FIG. 11)
  e) in acrylamide with addition of 0.5% of the copolymer PDMA-NIPAM prepared according to example 9, to the separation medium (FIG. 12).

Figure 9:
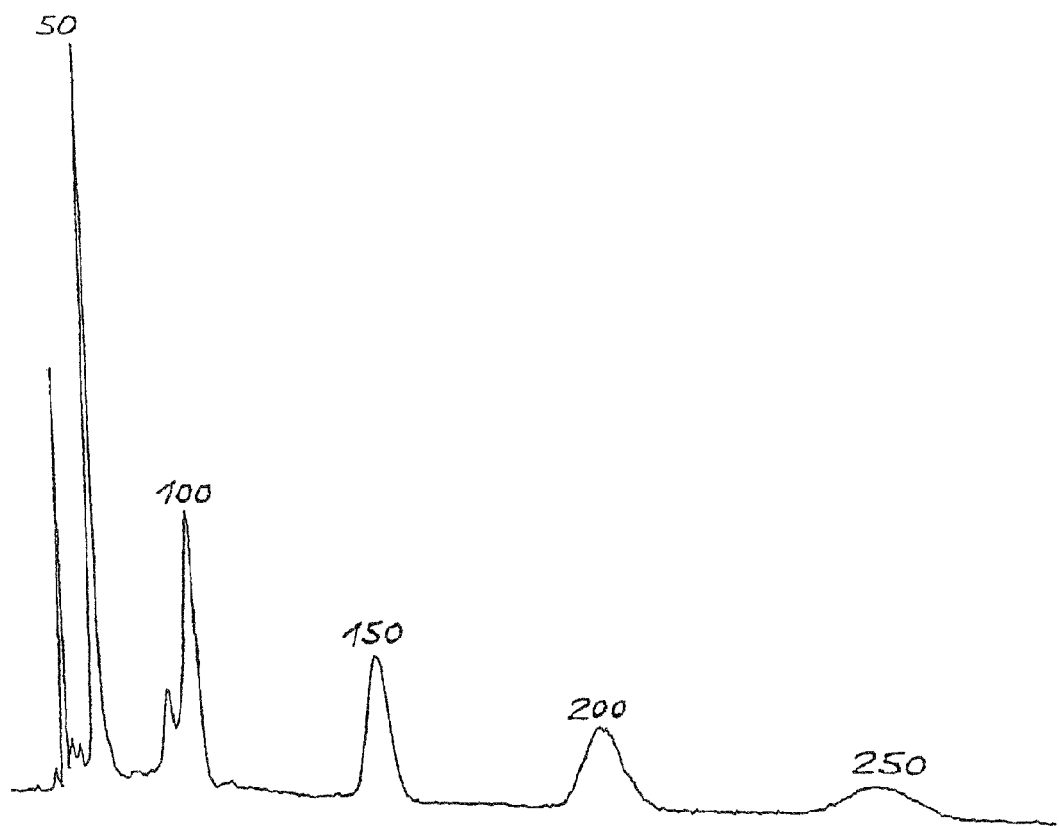
FIG. 9 is a control electropherogram representing a separation identical to that of FIG. 8, in a capillary pretreated for 2 hours with an aqueous solution containing 3% of triblock copolymer "pluronic F127" (BASF). The numbers above the peaks indicate the size of the corresponding DNA fragment.
Figure 10:
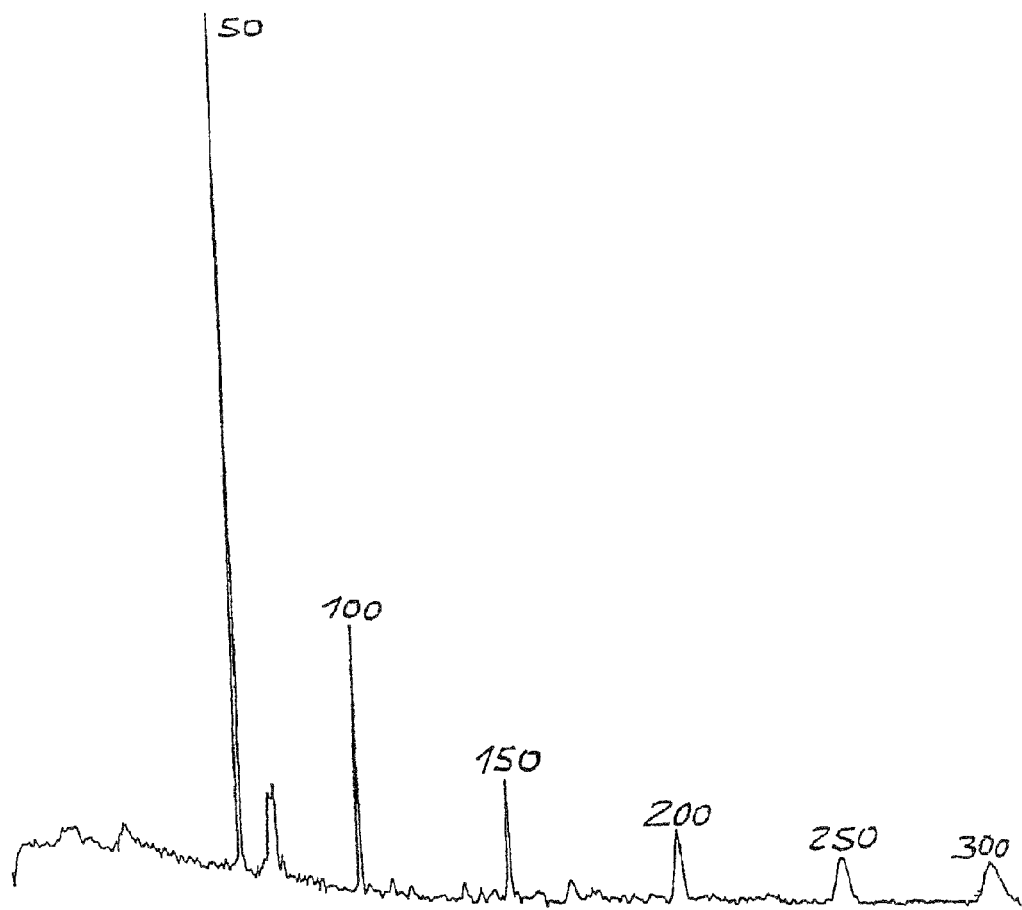
FIG. 10 is an electropherogram representing a separation identical to that of FIG. 8, in a capillary pretreated for 2 hours min with an aqueous solution containing 3% of comb polymer of the type having a hydroxyethylcellulose backbone, carrying side chains of the short alkyl chain type (NATROSOL PLUS 331, Aqualon). The numbers above the peaks indicate the size of the corresponding DNA fragment.

It is noted that the use of copolymers according to the invention considerably improves the sharpness of the peaks, whether this is in the form of treatment of the capillary before separation (FIGS. 10 and 11), or in the form of addition to the separation medium itself (FIG. 12). This augmentation, which is very marked with respect to the nontreated capillary (FIG. 8), is also significant with respect to a capillary treated with a commercial block copolymer which does not have the minimum number of polymer segments which characterize the invention (FIG. 9). Finally, it is also noted that the copolymers exhibiting side branches of high molecular mass and irregular length (FIGS. 11 and 12) lead to better separations than those exhibiting branches which are of low molecular mass and monodisperse (FIG. 10).

FIG. 14 represents the extrapolated resolution between peaks differing by one base, evaluated by interpolation from the results of the "Sizer 500". It is once again noted that this resolution is improved by the polymers according to the invention.

Example 13

Separation properties obtained for DNA (50-500 bp sizer, Pharmacia biotech), at 50° C. in an ABI 310 device (Perkin-Elmer), in a 50 mM Na TAPS buffer containing 2 mM EDTA and 7 M urea.

Figure 13A:
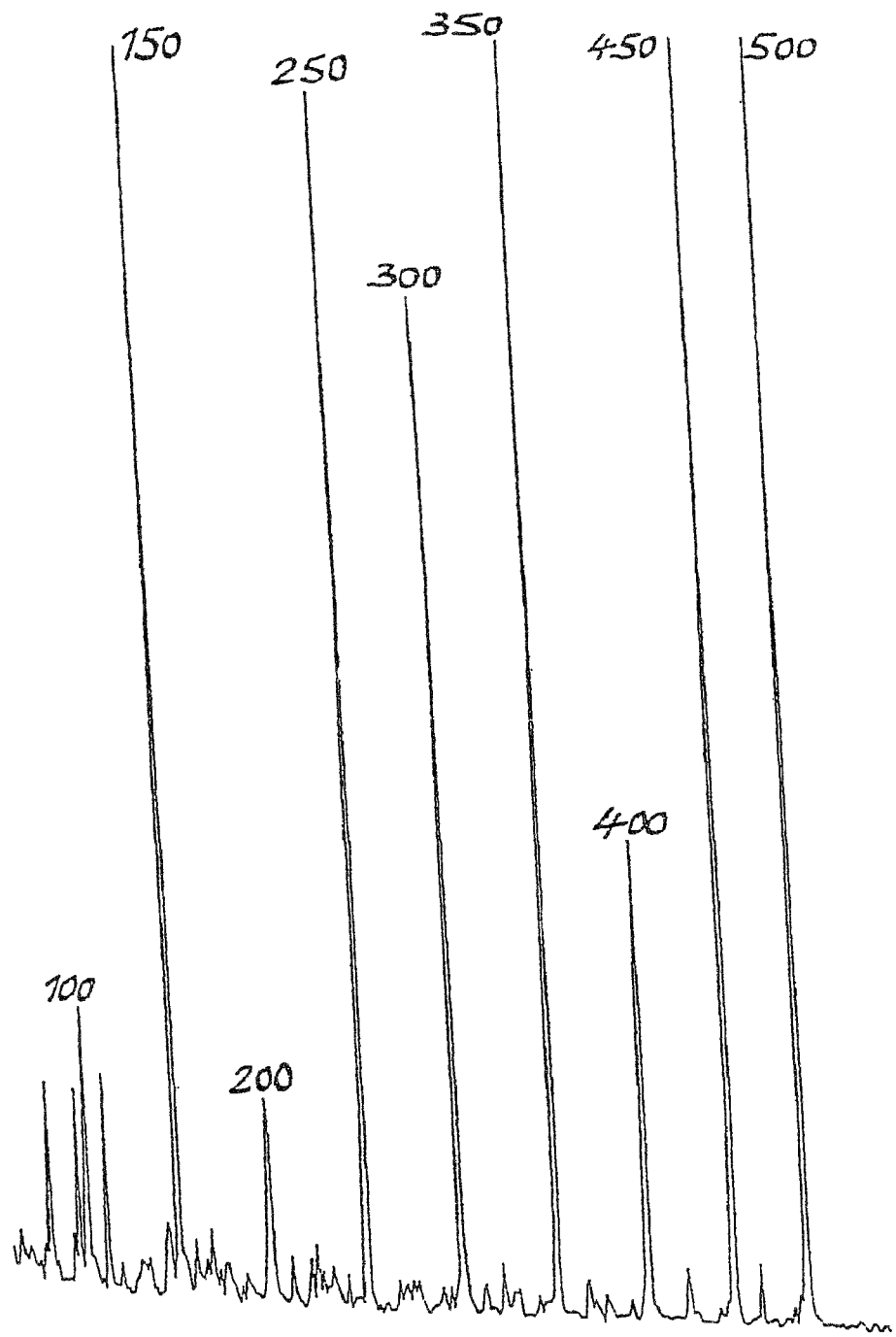
FIGS. 13a and 13b are electropherograms representing a separation identical to that of FIG. 9.
Figure 13B:
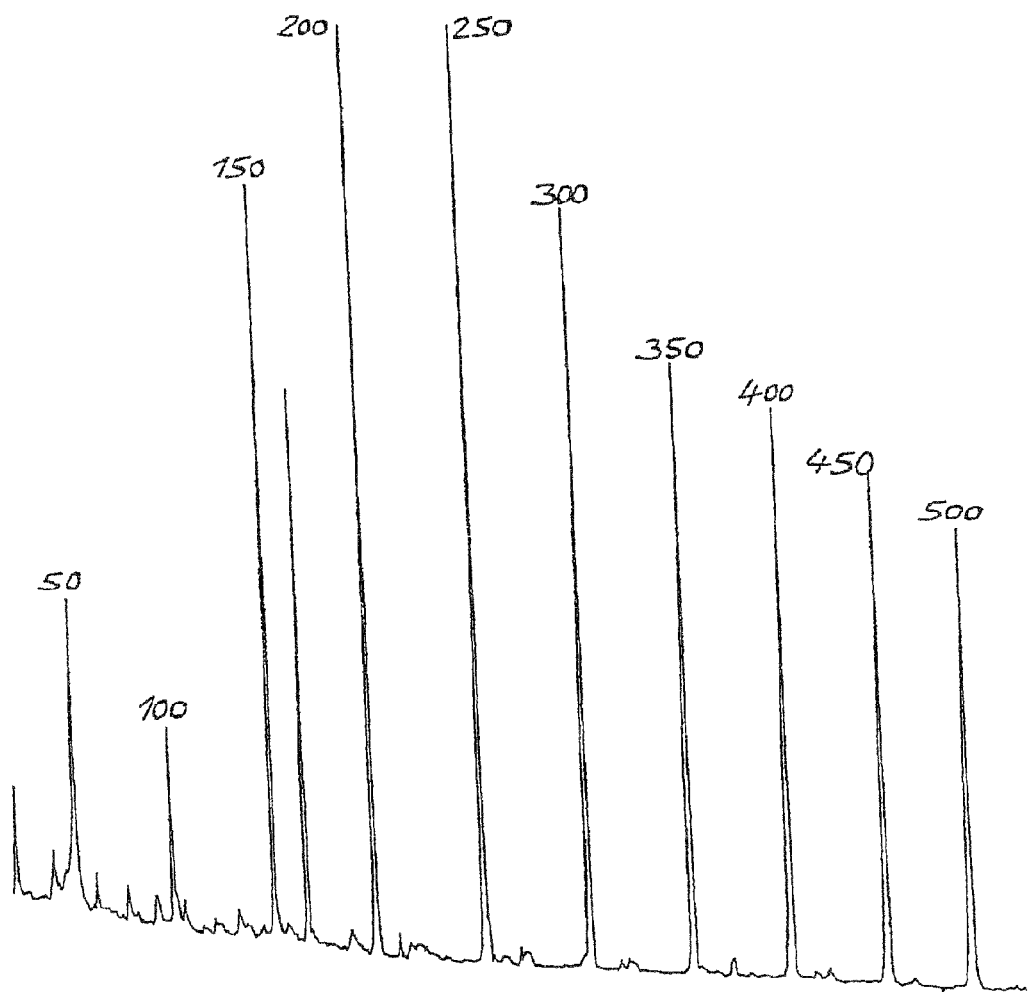

These properties are evaluated according to two variants:
a) in acrylamide with addition of 0.5% of the copolymer PAM-PDMA-1 prepared according to example 11, to the separation medium (FIG. 13a);
b) in acrylamide after treatment with the copolymer PAM-PDMA-1 prepared according to example 11 (FIG. 13b).

Compared with FIG. 8, it is once again noted that the use of this other copolymer according to the invention considerably improves the sharpness of the peaks, whether this is in the form of treatment of the capillary before separation or in the form of addition to the separation medium itself. This increase in performance is found in the measurement of the resolution, FIG. 14.

This sharpness of peaks is attributed to the property of the processes according to the invention, which makes it possible to reduce interaction of the analytes with the wall. The better performances obtained with the copolymers exhibiting polymer segments of high and irregular molecular mass are attributed to the formation of a thick and "flexible" adsorbed layer. Such a layer would make it possible to push the analytes away from the wall, while at the same time remaining very swollen with water and therefore relatively unlikely to give specific interactions with these analytes.

Example 14

Use of a surface treatment solution according to the invention in a microfluid cell.

A microfluid cell comprising a channel 20 μm thick and 100 μm wide is prepared with polydimethylsiloxane, as described in Ocvirk et al., Electrophoresis, 21, 107 (2000). The walls of the channel are treated by incubation for 30 min, a/ with a solution containing 3% of "Pluronics F127" and b/ with a solution containing 3% of polymers according to the invention PDMA-NIPAM, prepared according to example 9. In both cases, the channel is rinsed, then filled with a solution of magnetic particles and subjected to a magnetic field of 60 mTestla, as described in Mayer et al., Mat. Res. Soc. Symp. Proc. 463, 57 (1998). The presence of electroosmosis is tested by the movement of the magnetic particles, in an electric field of 20 V/cm. For the capillary treated with the Pluronics, this displacement appears after the field has been applied for 2 to 3 min. For the capillary treated with the polymer according to the invention, there is still no observable displacement after the field has been applied for 3 hours. The copolymer additives according to the invention thus provide the means for better control of the transport of a fluid or of species contained in this fluid, in microfluid channels which are varied in nature.

Example 15

Preparation of a Copolymer P(AM-PDMA)-2 Having an Acrylamide Backbone and PDMA Grafts, of Molecular Mass Approximately 3,000 kDalton The preparation is identical to that described in example 11, except for the concentration of $((NH_4)_2S_2O_8)$ [0.1 mol % instead of 0.075 mol % of the amount of monomers] and of $(Na_2S_2O_5)$ (0.015 mol % instead of 0.0225 mol % of the amount of monomers). The viscosity, given in FIG. 13, makes it possible to evaluate the molecular mass, which is of the order of 3,000 kDalton, from that of the p(AM-PDMA)-1, using the cubic dependency of the viscosity as a function of the molecular mass for entangled polymers.

Example 16

Preparation of a Copolymer P(AM-PDMA)-3 Bearing PDMA Grafts, of Molecular Mass Approximately 30,000

First, the macromonomer of molecular mass 30,000 is prepared as described in example 6, except for the Ro ratio, which is set at 0.015 instead of 0.03. This macromonomer is then polymerized with acrylamide, according to the protocol described in example 16.

Example 17

Evaluation of the performances of separation media incorporating a copolymer in accordance with the invention The polymers added in a proportion of 0.5% are:
poly(AM-PDMA)-1 prepared according to example 11,
poly(AM-PDMA)-2 prepared according to example 15,
poly(AM-PDMA)-3 prepared according to example 16,
poly(DMA-PNIPAM) prepared according to example 9, and
the linear PDMA homopolymer which represents the comparative test.

The results obtained are given in FIG. 15.

It is noted that the copolymers according to the invention produce performances comparable to or greater than those of the PDMA homopolymer, despite a much smaller fraction of monomers exhibiting a strong affinity for the wall. It is also noted that the polymers of higher molecular mass (poly(AM-PDMA)-2), and also those in which the grafts are of higher molecular mass (poly(AM-PDMA-3), produce the best resolution. On the other hand, the most hydrophobic polymer (poly(PDMA-NIPAM) produces the poorest resolution. In the particular case of poly(AM-PDMA)-2, 10 consecutive tests were carried out without intermediate regeneration of the walls of the channel.

Advantageously, no decrease in performances is observed.

It is important to note that the linear PDMA homopolymer does not make it possible to obtain such results.

The invention claimed is:

1. An aqueous liquid medium for analyzing, purifying or separating species inside an element comprising walls or for treating the walls of said element, comprising:
   at least one polymer having several polymer segments that differ in chemical or topological nature, said at least one polymer being one of:
   (a) an irregular block copolymer
   and
   (b) an irregular comb polymer having a polydispersity of at least 1.5 for all polymer segments of at least one chemical or topological nature and having side branches with a molecular mass greater than 1500; and
   a viscosity that does not vary by a factor of 2 or more over a temperature range of 20° C. or less between a temperature that is 10° C. higher than the solidification point of said medium and a temperature that is 10° C. lower than the boiling point of said medium,
   wherein
   said at least one polymer has an average of at least three junction points established between polymer segments that differ in chemical or topological nature.

* * * * *